(12) United States Patent
Kalvakolanu et al.

(10) Patent No.: US 11,560,412 B2
(45) Date of Patent: Jan. 24, 2023

(54) COMPOSITIONS COMPRISING GRIM-19 THERAPEUTICS AND METHODS OF USE

(71) Applicants: Dhan Kalvakolanu, Sykesville, MD (US); Shreeram Nallar, Baltimore, MD (US)

(72) Inventors: Dhan Kalvakolanu, Sykesville, MD (US); Shreeram Nallar, Baltimore, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 513 days.

(21) Appl. No.: 15/476,787

(22) Filed: Mar. 31, 2017

(65) Prior Publication Data

US 2017/0298108 A1    Oct. 19, 2017

Related U.S. Application Data

(60) Provisional application No. 62/317,029, filed on Apr. 1, 2016.

(51) Int. Cl.
| | | |
|---|---|---|
| *A61K 38/17* | (2006.01) | |
| *C07K 14/435* | (2006.01) | |
| *A61P 35/00* | (2006.01) | |
| *C12Q 1/68* | (2018.01) | |
| *C07K 14/47* | (2006.01) | |
| *C12Q 1/6886* | (2018.01) | |
| *A61K 48/00* | (2006.01) | |

(52) U.S. Cl.
CPC ...... *C07K 14/4703* (2013.01); *A61K 38/1709* (2013.01); *C07K 14/4747* (2013.01); *C12Q 1/6886* (2013.01); *A61K 48/00* (2013.01); *C07K 2319/10* (2013.01); *C07K 2319/21* (2013.01); *C07K 2319/23* (2013.01); *C07K 2319/40* (2013.01); *C07K 2319/41* (2013.01); *C07K 2319/43* (2013.01); *C07K 2319/50* (2013.01); *C12N 2740/16043* (2013.01); *C12Q 2600/106* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| 4,722,848 A | 2/1988 | Paoletti | |
|---|---|---|---|
| 2016/0367627 A1* | 12/2016 | Khodarev | A61K 31/506 |

FOREIGN PATENT DOCUMENTS

| WO | 94/26914 A1 | 11/1994 |
|---|---|---|
| WO | 95/00655 A1 | 1/1995 |
| WO | 95/02697 A1 | 1/1995 |
| WO | 95/16772 A1 | 6/1995 |
| WO | 95/23867 A1 | 9/1995 |
| WO | 95/25071 A1 | 9/1995 |

OTHER PUBLICATIONS

Vaishya et al, Long-term delivery of protein therapeutics, Expert Opinion on Drug Delivery, 2014, 12:3, 415-440.*
Song et al, STAT signaling in head and neck cancer, Oncogene, 2000, pp. 2489-2495.*
Angell et al, Identification of GRIM-19, a Novel Cell Death-regulatory Gene Induced by the Interferon-b and Retinoic Acid Combination, Using a Genetic Approach, JBC, 2000, pates 33416-33426.*
Akash et al, Development of therapeutic proteins: Advances and challenges, Turkish Journal of Biology 39(3) ■ Jan. 2015, pp. 1-17.*
Bruno et al, Basics and recent advances in peptide and protein drug delivery, Ther Deliv. Nov. 2013; 4(11): 1443-1467.*
Shanks et al, Are animal models predictive for humans? Philosophy, Ethics, and Humanities in Medicine, 2009, pp. 1-20.*
Liu et al, Recent Advances in Anti-cancer Protein/Peptide Delivery, : Bioconjugate Chem. 2019, 30, 305-324.*
Habault and Poyet, Recent Advances in Cell Penetrating Peptide-Based Anticancer Therapies, Molecules 2019, 24, pp. 1-17.*
Briolay et al, Delivery of cancer therapies by synthetic and bio-inspired nanovectors, Molecular Cancer (2021), pp. 1-24.*
Rosenblum, Progress and challenges towards targeted delivery of cancer therapeutics, Nature Communications, 2018, pp. 1-12.*
Moreira et al, GRIM-19 function in cancer development, Mitochondrion, 2010, pp. 693-699.*
Roomi et al, Patterns of MMP-2 and MMP-9 expression in human cancer cell lines, Oncology Reports 21: 1323-1333, 2009.*
Liu et al, Activation of STAT3 is involved in malignancy mediated by CXCL12-CXCR4 signaling in human breast cancer, Oncology Reports 32: 2760-2768, 2014.*
Cheng et al., Overexpression of CXCL1 and its receptor CXCR2 promote tumor invasion in gastric cancer, Annals of Oncology 22: 2267-2276, 2011.*
Gresser, Endogenous type I interferons as a defense against tumors, Cytokine Growth Factor Rev, 13:111-118 (2002).
Dunn, Interferons, immunity and cancer immunoediting, Nat. Rev Immunol, 6:836-848 (2006).
Legrier, Activation of IFN/STAT1 signalling predicts response to chemotherapy in oestrogen receptor-negative breast cancer, Br J Cancer, 114:177-187 (2016).
Xia, Porous Silicon Microparticle Potentiates Anti-Tumor Immunity by Enhancing Cross-Presentation and Inducing Type I Interferon Response, Cell Reports, 11:957-966 (2015).

(Continued)

*Primary Examiner* — Maria Marvich
(74) *Attorney, Agent, or Firm* — Nevrivy Patent Law Group P.L.L.C.

(57) ABSTRACT

The present invention provides nucleic acids encoding a fusion protein comprising a nucleotide sequence encoding GRIM-19 or a biologically active fragment or derivative thereof and a nucleotide sequence encoding a protein transduction domain. Proteins encoded by the nucleic acids, pharmaceutical compositions and methods of treatment are also provided. The invention also provides viral vectors comprising GRIM-19 or a biologically active fragment or derivative thereof, pharmaceutical compositions and methods of treatment using the same.

3 Claims, 10 Drawing Sheets

Specification includes a Sequence Listing.

(56) References Cited

OTHER PUBLICATIONS

Shen, Genome-Derived Cytosolic DNA Mediates Type I Interferon-Dependent Rejection of B Cell Lymphoma Cells, Cell Reports, 11:460-473 (2015).
Sistigu, Cancer cell-autonomous contribution of type I interferon signaling to the efficacy of chemotherapy, Nat Med, 20:1301-1312 (2014).
Deng, STING-dependent Cytosolic DNA Sensing Promotes Radiation-induced Type I interferon-dependent Antitumor Immunity in Immunogenic Tumors, Immunity, 41:843-852 (2014).
Nagai, Disabling of the erbB Pathway Followed by IFN-gamma Modifies Phenotype and Enhances Genotoxic Eradication of Breast Tumors, Cell reports, 12:2049-2059 (2015).
Critchley-Thorne, Impaired interferon signaling is a common immune defect in human cancer, Proc Natl Acad Sci USA, 106:9010-9015 (2009).
Borden, Interferons at age 50: past, current and future impact on biomedicine, Nature reviews, Drug discovery, 6:975-990 (2007).
Kalvakolanu, The GRIMs: a new interface between cell death regulation and interferon/retinoid induced growth suppression, Cytokine Growth Factor Rev, 15:169-194 (2004).
Seo, Viral Interferon Regulatory Factor 1 of Kaposi's Sarcoma-Associated Herpesvirus Interacts with a Cell Death Regulator, GRIM19, and Inhibits Interferon/Retinoic Acid-Induced Cell Death, J Virol, 76:8797-8807 (2002).
Sun, GRIM-19 inhibits v-Src-induced cell motility by interfering with cytoskeletal restructuring, Oncogene, 28:1339-1347 (2009).
Zhou, GRIM-19 Disrupts E6/E6AP Complex to Rescue p53 and Induce Apoptosis in Cervical Cancers, PLoS One, 6:1-12 (2011).
Zhang, The cell death regulator GRIM-19 is an inhibitor of signal transducer and activator of transcription 3, Proc Natl Acad Sci USA, 100:9342-9347 (2003).
Lufei, GRIM-19, a death-regulatory gene product, suppresses Stat3 activity via functional interaction, Embo J, 22:1325-1335 (2003).
Squarize, Molecular Cross-Talk between the NFKB and STAT3 Signaling Pathways in Head and Neck Squamous Cell Carcinoma, Neoplasia, 8:733-746 (2006).
Suiqing, Overexpression of Phosphorylated-STAT3 Correlated with the Invasion and Metastasis of Cutanaeous Squamous Cell Carcinoma, J Dermatol, 32:354-360 (2005).
Xi, Src Kinases Mediate STAT Growth Pathways in Squamous Cell Carcinoma of the Head and Neck*, J Biol Chem, 278:31574-31583 (2003).
Chan, Disruption of Stat3 reveals a critical role in both the initiation and the promotion stages of epithelial carcinogenesis, J Clin Invest, 114:720-728 (2004).
Pedranzini, Stat3 is required for the development of skin cancer, J Clin Invest, 114:619-622 (2004).
Inghirami, New and Old Functions of STAT3: A Pivitol Target for Individualized Treatment of Cancer, Cell Cycle, 4:1131-1133 (2005).
Yu, STATs in cancer inflammation and immunity: a leading role for STAT3, Nat Rev Cancer, 9:798-809 (2009).
Gong, Correlations of GRIM-19 and its target gene product STAT3 to malignancy of human colorectal carcinoma, Ai Zheng, 26:683-687 (2007).
Zhang, Effects of Plasmid-Based Stat3-Specific Short Hairpin RNA andGRIM-19 on PC-3M Tumor Cell Growth, Clin Cancer Res, 14:559-568 (2008).
Zhou, Expression and clinical significance of GRIM-19 in non-small cell lung cancer, Ai Zheng, 28:431-435 (2009).
Zhou, Down-Regulation of GRIM-19 Expression Is Associated With Hyperactivation of STAT3-Induced Gene Expression and Tumor Growth in Human Cervical Cancers, J Interferon Cytokine Res, 29:695-703 (2009).
Okamoto, Overexpression of GRIM-19 in Cancer Cells Suppresses STAT3-Mediated Signal Transduction and Cancer Growth, Mol Cancer Ther, 9:2333-2343 (2010).
Hao, Depletion of GRIM-19 Accelerates Hepatocellular Carcinoma Invasion Via Inducing EMT and Loss of Contact Inhibition, J Cell Physiol, 227:1212-1219 (2012).
Zhang, Downregulation of GRIM-19 promotes growth and migration of human glioma cells, Cancer Sci, 102:1991-1999 (2011).
Fan, Expression and clinical significance of GRIM-19 in lung cancer, Med Oncol, 29:3183-3189 (2012).
Li, Downregulation of GRIM-19 is associated with hyperactivation of p-STAT3 in hepatocellular carcinoma, Med Oncol, 29:3046-3054 (2012).
Nallar, Tumor-derived Mutations in the Gene Associated with Retinoid Interferon-induced Mortality (GRIM-19) Disrupt Its Antisignal Transducer and Activator of Transcription 3 (STAT3) Activity and Promote Oncogenesis, J Biol Chem, 288:7930-7941 (2013).
Maximo, Somatic and germline mutation in GRIM-19, a dual function gene involved in mitochondrial metabolism and cell death, is linked to mitochondrion-rich (Hurthle cell) tumours of the thyroid, Br J Cancer, 92:1892-1898 (2005).
Nallar, Identification of a Structural Motif in the Tumor-Suppressive Protein GRIM-19 Required for Its Antitumor Activity, Am J Pathol, 177:896-907 (2010).
Morris, Genomic dissection of the epidermal growth factor receptor (EGFR)/PI3K pathway reveals frequent deletion of the EGFR phosphatase PTPRS in head and neck cancers, Proc Natl Acad Sci USA, 108:19024-19029 (2011).
Zini, Oral cancer over four decades: epidemiology, trends, histology, and survival by anatomical sites, J Oral Pathol Med, 39:299-305 (2010).
Rothenberg, The molecular pathogenesis of head and neck squamous cell carcinoma, J Clin Invest, 122:1951-1957 (2012).
Schlecht, Effect of Smoking Cessation and Tabacco Type on the Risk of Cancers of the Upper Aero-Digestive Tract in Brazil, Epidemiology, 10:412-418 (1999).
Schlecht, Interaction between Tobacco and Alcohol Consumption and the Risk of Cancers of the Upper AeroDigestive Tract in Brazil, American Journal of Epidemiology, 150:1129-1137 (1999).
Sturgis, Trends in Head and Neck Cancer Incidence in Relation to Smoking Prevalence, Cancer, 110:429-1435 (2007).
Hashibe, Alcohol Drinking in Never Users of Tobacco, CigaretteSmoking in Never Drinkers, and the Risk of Head and Neck Cancer: Pooled Analysis in the International Head and Neck Cancer Epidemiology Consortium, J Natl Cancer Inst, 99:777-789 (2007).
Pelucchi, Alcohol and tobacco use, and cancer risk for upper aerodigestive tract and liver, Eur J Cancer Prev, 17:340-344 (2008).
Bose, Head and neck cancer: from anatomy to biology, Int J Cancer, 133:2013-2023 (2013).
Kalakonda, Tumor Suppressive Protein Gene Associated with Retinoid-Interferon-Induced Mortality (GRIM)-19 Inhibits src-Induced Oncogenic Transformation at Multiple Levels, Am J Pathol, 171:1352-1368 (2007).
Zhang, Intratumoral Delivery and Suppression of Prostate Tumor Growth by Attenuated *Salmonella enterica* serovar typhimurium Carrying Plasmid-Based Small Interfering RNAs, Cancer Res, 67:5859-5864 (2007).
Czerninski, Targeting Mammalian Target of Rapamycin by Rapamycin Prevents Tumor Progression in an Oral-Specific Chemical Carcinogenesis Model, Cancer Prev Res (Phila), 2:27-36 (2009).
Vitale-Cross, Chemical Carcinogenesis Models for Evaluating Molecular-Targeted Prevention and Treatment of Oral Cancer, Cancer Prev Res (Phila), 2:419-422 (2009).
Wong, Oral-Specific Chemical Carcinogenesis in Mice: An Exciting Model for Cancer Prevention and Therapy, Cancer Prev Res (Phila), 2:10-13 (2009).
Chidambaram, Chromosomal Localization of Human GRIM-19, a Novel IFN-B and Retinoic Acid-Activated Regulator of Cell Death, J Interferon Cytokine Res, 20:661-665 (2000).

* cited by examiner

The GRIM-19<sup>-ve</sup> signature: UP: CCL-5, -22, CXCLs -1,-2, -3,-4,-5, -7, -9, -10,-11,-12,-13,-14,-15,-16,-17 CX3CL1, CXCR -2,-3,-5 -6-7; IL-5, IL-17B and IL-12B, TNFSF14 (LIGHT), EGFR, Fyn oncogene, Matrix metalloproteases (MMP) 2,7,9,19, 20, 23, and 24. Down: CCL-2, -14,-15, CCR -4,-7, -9 and CXCR4; IL-1 and IL36.

Open reading frame of Cell-Penetrating Peptide (CPP)-tagged AcGFP. (Baculoviral expression)

```
ATGGCACATCATCATCATCATCATGTGGGTACCGGTTCGAATGATGACGACGACAAGAGT  < 60
 M  A  H  H  H  H  H  H  V  G  T  G  S  N  D  D  D  D  K  S

CCGGATAGACGAAGGCGCAGACGGAGGCGTAGACCGTCTGCCAGCTATCCATACGACGTG  < 120
 P  D  R  R  R  R  R  R  R  R  P  S  A  S  Y  P  Y  D  V

CCTGACTACGCGAGGCTGCAATTCATGGTGAGCAAGGGCGCTGAGCTGTTCACCGGCATC  < 180
 P  D  Y  A  R  L  Q  F  M  V  S  K  G  A  E  L  F  T  G  I

GTGCCCATCCTGATCGAGCTGAATGGCGATGTGAATGGCCACAAGTTCAGCGTGAGCGGC  < 240
 V  P  I  L  I  E  L  N  G  D  V  N  G  H  K  F  S  V  S  G

GAGGGCGAGGGCGATGCCACCTACGGCAAGCTGACCCTGAAGTTCATCTGCACCACCGGC  < 300
 E  G  E  G  D  A  T  Y  G  K  L  T  L  K  F  I  C  T  T  G

AAGCTGCCTGTGCCCTGGCCAACCTTGGTGACCACCCTGAGCTACGGCGTGCAGTGCTTC  < 360
 K  L  P  V  P  W  P  T  L  V  T  T  L  S  Y  G  V  Q  C  F

TCACGCTACCCCGATCACATGAAGCAGCACGACTTCTTCAAGAGCGCCATGCCTGAGGGC  < 420
 S  R  Y  P  D  H  M  K  Q  H  D  F  F  K  S  A  M  P  E  G

TACATCCAGGAGCGCACCATCTTCTTCGAGGATGACGGCAACTACAAGTCGCGCGCCGAG  < 480
 Y  I  Q  E  R  T  I  F  F  E  D  D  G  N  Y  K  S  R  A  E

GTGAAGTTCGAGGGCGATACCCTGGTTAATCGCATCGAGCTGACCGGCACCGATTTCAAG  < 540
 V  K  F  E  G  D  T  L  V  N  R  I  E  L  T  G  T  D  F  K

GAGGATGGCAACATTCTGGGCAATAAGATGGAGTACAACTACAACGCCCACAATGTGTAC  < 600
 E  D  G  N  I  L  G  N  K  M  E  Y  N  Y  N  A  H  N  V  Y

ATTATGACCGACAAGGCCAAGAATGGCATCAAGGTGAACTTCAAGATCCGCCACAACATT  < 660
 I  M  T  D  K  A  K  N  G  I  K  V  N  F  K  I  R  H  N  I

GAGGATGGCAGCGTGCAGCTGGCCGACCACTACCAGCAGAATACCCCCATCGGCGATGGC  < 720
 E  D  G  S  V  Q  L  A  D  H  Y  Q  Q  N  T  P  I  G  D  G

CCTGTGCTGCTGCCCGATAACCACTACCTGTCCACCCAGAGCGCCCTGTCCAAGGACCCC  < 780
 P  V  L  L  P  D  N  H  Y  L  S  T  Q  S  A  L  S  K  D  P

AACGAGAAGCGCGATCACATGATCTATTTCGGCTTCGTGACCGCCGCCGCCATCACCCAC  < 840
 N  E  K  R  D  H  M  I  Y  F  G  F  V  T  A  A  A  I  T  H

GGCATGGATGAGCTGTACAAGTAG  < 864   SEQ ID NO: 58
 G  M  D  E  L  Y  K  ***        SEQ ID NO: 59
```

FIG. 9

Open reading frame of Cell-Penetrating Peptide (CPP)-tagged human GRIM-19 (bacterial expression)

```
ATGGCA......................GTGGGTACCGGTTCGAATGATGACGACGACAAGAGT  < 60
 M  A  H  H  H  H  H  H  V  G  T  G  S  N  D  D  D  D  K  S

CCGGATAGACGAAGGCGCAGAACGGAGGCGTAGACCGTCTGCCAGCTATCCATACGACGTG    < 120
 P  D  R  R  R  R  R  R  R  R  P  S  A  S  Y  P  Y  D  V

CCTGACTACGCGAGGCTGCAATTC..................................       < 180
 P  D  Y  A  R  L  Q  F  M  A  A  S  K  V  K  Q  D  M  P  P

...........................................................     < 240
 P  G  G  Y  G  P  I  D  Y  K  R  N  L  P  R  R  G  L  S  G

...........................................................     < 300
 Y  S  M  L  A  I  G  I  G  T  L  I  Y  G  H  W  S  I  M  K

...........................................................     < 360
 W  N  R  E  R  R  R  L  Q  I  E  D  F  E  A  R  I  A  L  L

...........................................................     < 420
 P  L  L  Q  A  E  T  D  R  R  T  L  Q  M  L  R  E  N  L  E

...........................................................     < 480
 E  E  A  I  I  M  K  D  V  P  D  W  K  V  G  E  S  V  F  H

...........................................................     < 540
 T  T  R  W  V  P  P  L  I  G  E  L  Y  G  L  R  T  T  E  E

.................................              < 579   SEQ ID NO: 10
 A  L  H  A  S  H  G  F  M  W  Y  T  ***                SEQ ID NO: 12
```

FIG. 10

Open reading frame of Myc epitope-tagged human GRIM-19. (Lentiviral vector)

```
ATGGCGGCTTCAAAGGTTAAGCAGGACATGCCTCCGCCTGGGTACGGCCCTATCGAC  < 60
 M  A  A  S  K  V  K  Q  D  M  P  P  P  G  Y  G  P  I  D

TACAAGCGGAATTTGCCCCGTCGAGGACTGTCCGGCTACAGCATGCTCGCCATACGGATT  < 120
 Y  K  R  N  L  P  R  R  G  L  S  G  Y  S  M  L  A  I  G  I

GGAACCTTGATCTACCGCCACTGGAGCATAATGAAGTGGAACCGTGAGCGCCGCCGCCTA  < 180
 G  T  L  I  Y  G  H  W  S  I  M  K  W  N  R  E  R  R  R  L

CAAATCGAGGACTTCGAGGCTCGGATCGCTCTGTTGCCACTGTTACAGGCAGAAACGGAC  < 240
 Q  I  E  D  F  E  A  R  I  A  L  L  P  L  L  Q  A  E  T  D

CGGAGAACCTTGCAGATGCTTCGGGAGAACCTGGAGGAGGCCATCATCATGAAGGAC     < 300
 R  R  T  L  Q  M  L  R  E  N  L  E  E  A  I  I  M  K  D

GTGCCCGACTGGAAGGTGGGAGTCTTGTTCACACAACCCTGGGTGCCGCCCTTG        < 360
 V  P  D  W  K  V  G  E  S  V  F  H  T  T  R  W  V  P  L

ATTGGGGAGCTGTACGGCCTGCGAACTACAGAAGAAGCTCTCATGCAGTACGGCTTC     < 420
 I  G  E  L  Y  G  L  R  T  T  E  E  A  L  H  A  S  H  G  F

ATGTGGTACACGGGATCCGCGGCCGCCAACGAAAACCTGTACTTCCAGAGCATCGCG     < 480
 M  W  Y  T  G  S  A  A  A  E  Q  K  L  I  S  E  E  D  L  A

GCCGCATAG    < 489    SEQ ID NO: 56
 A  A  ***           SEQ ID NO: 57
```

COMPOSITIONS COMPRISING GRIM-19 THERAPEUTICS AND METHODS OF USE

CROSS-REFERENCE TO RELATED APPLICATIONS

This application claims the benefit of U.S. Provisional Appl. No. 62/317,029, filed on Apr. 1, 2016, the contents of which are hereby incorporated by reference in their entirety.

STATEMENT OF FEDERALLY SPONSORED RESEARCH AND DEVELOPMENT

This invention was made with government support under Grant Number CA105005 awarded by the National Institutes of Health. The government has certain rights in the invention.

INCORPORATION-BY-REFERENCE OF MATERIAL SUBMITTED ELECTRONICALLY

Incorporated by reference in its entirety herein is a computer-readable sequence listing submitted concurrently herewith and identified as follows: One 25,250 Byte ASCII (Text) file named "Sequence_listing.txt," created on Mar. 31, 2017.

FIELD OF THE INVENTION

The field of the invention relates to medicine and pharmaceuticals, particularly methods and compositions for treating cancer.

BACKGROUND

The IFN-family of cytokines act as sentinels to prevent and eliminate tumor development (Gresser et al., Cytokine Growth Factor Rev 13: 111-118, 2002; Dunn et al., Nat Rev Immunol 6, 836-848, 2006). A number of recent reports indicate that the success of conventional chemotherapeutics, targeted anticancer agents, radiotherapy and immunotherapy relies on type I IFN signaling in vivo (Legrier et al., Br J Cancer 114: 177-187, 2016; Xia et al., Cell reports 11: 957-966, 2015; Shen et al., Cell reports 11: 460-473, 2015; Sistigu et al., Nat Med 20: 1301-1309, 2014; Deng et al., Immunity 41: 843-852, 2014; Nagai et al., Cell reports 12: 2049-2059, 2015). As a result, several human cancers accumulate IFN-signaling defects to escape from growth-suppression (Critchley-Thorne et al., Proc Natl Acad Sci USA 106: 9010-9015, 2009). IFNs inhibit tumor growth as efficiently as many clinically used therapeutics (Borden et al., Nature reviews. Drug discovery 6: 975-990, 2007), and their activity is further augmented when combined with other therapeutics including the retinoids (Kalvakolanu, D. V., Cytokine Growth Factor Rev 15: 169-194, 2004), a class of vitamin-A metabolites and synthetic derivatives. Since IFN/RA exerts a robust tumor suppression (Moore et al., (1994), Semin Hematol 31: 31-37; Shin et al., (2002), J Clin Oncol 20:364-370; Shin et al., (2001), J Clin Oncol 19, 3010-3017), whole genome expression knockdown strategies have been applied to identify IFN/RA target genes. One such protein that was identified, Gene-associated with Retinoid-IFN induced Mortality-19 (GRIM-19), binds to and blocks several viral and cellular oncogenes; foremost of which is the oncogenic transcription factor STAT3 (Seo et al., (2002), J Virol 76, 8797-8807; Sun et al., (2009), Oncogene 28, 1339-1347; Zhou et al., (2011), PLoS One 6, e22065; Zhang et al., (2003), Proc Natl Acad Sci USA 100, 9342-9347; Lufei et al., (2003), Embo J 22, 1325-1335). Distinct from its physiological functions, STAT3 is required for tumor development in humans and mice (Squarize et al., (2006), Neoplasia 8, 733-746; Suiqing et al., (2005), J Dermatol 32, 354-360; Xi et al., (2003), J Biol Chem 278, 31574-31583; Chan et al., (2004), J Clin Invest 114, 720-728; Pedranzini et al., (2004), J Clin Invest 114, 619-622). Persistently-active STAT3 stimulates angiogenesis, immune suppression, oncogenic inflammation, and metastases, and promotes the expression pro-cell cycle and anti-apoptotic proteins (Inghirami et al., (2005), Cell Cycle 4, 1131-1133; Yu et al., (2009), Nat Rev Cancer 9, 798-809).

A loss of GRIM-19 expression in a variety of primary human cancers of the kidney (80%), colon (25%), brain (60%), liver (65%), prostate (90%), lung (80%), and cervix (75%) has been documented (Gong et al., (2007), Ai Zheng 26, 683-687; Zhang et al., (2008), Clin Cancer Res 14, 559-568; Zhou et al., (2009), Ai Zheng 28, 431-435; Zhou et al., (2009), J Interferon Cytokine Res 29, 695-703; Okamoto et al., (2010), Mol Cancer Ther 9, 2333-2343; Hao et al., (2012), J Cell Physiol 227, 1212-1219; Zhang et al., (2011), Cancer Sci 102, 1991-1999; Fan et al., (2012), Med Oncol 29, 3183-3189; Li et al., (2012), Med Oncol 29, 3046-3054). More recently, functionally-inactivating somatic GRIM-19 mutations in HNSCCs and others in thyroid tumors have been identified (Nallar et al., (2013), J Biol Chem 288, 7930-7941; Maximo et al., (2005), Br J Cancer 92, 1892-1898). GRIM-19 mutants have been described from patients who developed lymph node metastases, failed to control STAT3 activity, and which promoted tumor growth and metastases (Nallar et al., (2013), J Biol Chem 288, 7930-7941; Nallar et al., (2010), Am J Pathol 177, 896-907). Exogenous administration of GRIM-19 through plasmid based vectors suppressed tumor growth (Deng et al., Immunity 41: 843-852, 2014).

A broad locus at chr19p13 is deleted in 32% of the oral tumors, which harbors GRIM-19 (19p13.2) (Morris et al., (2011), Proc Natl Acad Sci USA 108, 19024-19029; Chidambaram et al., (2000), J Interferon Cytokine Res 20, 661-665). In addition, publicly available databases report at least 50 different point mutations and several deletions from various primary human cancers. Using knockout mice, it was shown that even a mono-allelic loss of GRIM-19 was sufficient to promote carcinogen-induced SCC development (Sistigu et al., Nat Med 20: 1301-1309, 2014).

Head and neck squamous cell carcinoma (HNSCC) is on the rise at annual rates from 4% to as much as 10% in recent years. Annually, 50,000 and 600,000 new cases are diagnosed in the US and around the world, respectively (Zini et al., (2010), J Oral Pathol Med 39, 299-305; Rothenberg et al., (2012), J Clin Invest 122, 1951-1957). About 50% of advanced HNSCC recur within 2 years. HPV infection, tobacco usage are the major risk factors for HNSCC development and alcohol consumption further increases it (Schlecht et al., (1999), Epidemiology 10, 412-418; Schlech et al., (1999), American Journal of Epidemiology 150, 1129-1137; Sturgis et al., (2007), Cancer 110, 1429-1435; Hashibe et al., (2007), J Natl Cancer Inst 99, 777-789; Pelucchi et al., (2008), Eur J Cancer Prev 17, 340-344; Bose et al., (2013), Int J Cancer 133, 2013-2023). The mechanisms and genetic alterations in HNSCC are more complex and varied. Targeted therapeutic drug such as cetuximab (anti-EGFR antibody) prolongs the survival of HNSSC patients by 25% (Suiqing et al., (2005), J Dermatol 32, 354-360). However, drug resistance develops posing limitation of this drug. Thus, there is a critical need to develop new therapeutics to treat HNSCC as well as other cancers.

This background information is provided for informational purposes only. No admission is necessarily intended, nor should it be construed, that any of the preceding information constitutes prior art against the present invention.

SUMMARY

It is to be understood that both the foregoing general description of the embodiments and the following detailed description are exemplary, and thus do not restrict the scope of the embodiments.

According to non-limiting example embodiments, in one aspect, the invention provides a nucleic acid molecule encoding a fusion protein comprising
   i) a nucleotide sequence encoding GRIM-19 or a biologically active fragment or derivative thereof; and
   ii) a nucleotide sequence encoding a protein transduction domain.

In another aspect, the invention provides a fusion protein comprising
   i) GRIM-19 or a biologically active fragment or derivative thereof; and
   ii) a protein transduction domain.

In another aspect, the invention provides a pharmaceutical composition comprising a fusion protein comprising
   i) GRIM-19 or a biologically active fragment or derivative thereof; and
   ii) a protein transduction domain.
and one or more pharmaceutically acceptable excipients.

In another aspect, the invention provides a viral vector encoding GRIM-19 or a biologically active fragment or derivative thereof.

In another aspect, the invention provides a pharmaceutical composition comprising a viral vector encoding GRIM-19 or a biologically active fragment or derivative thereof, and one or more pharmaceutically acceptable excipients.

In another aspect, the invention provides a method of treating cancer comprising administering to a subject in need thereof an effective amount of a pharmaceutical composition comprising
   i) GRIM-19 or a biologically active fragment or derivative thereof; and
   ii) a protein transduction domain.

In another aspect, the invention provides a method of treating cancer comprising administering to a subject in need thereof an effective amount of a pharmaceutical composition comprising a viral vector encoding GRIM-19 or a biologically active fragment or derivative thereof.

In another aspect, the invention provides a method of treating an autoimmune disease comprising administering to a subject in need thereof an effective amount of a pharmaceutical composition comprising
   i) GRIM-19 or a biologically active fragment or derivative thereof; and
   ii) a protein transduction domain.

In another aspect, the invention provides a method of treating an autoimmune disease comprising administering to a subject in need thereof an effective amount of a pharmaceutical composition comprising a viral vector encoding GRIM-19 or a biologically active fragment or derivative thereof.

In another aspect, the invention provides a method of predicting responsiveness of a subject having a disease or condition to GRIM-19 treatment, comprising obtaining the results of an assay from a tissue from the subject that measures the expression level of one or more of CCL-5, CCL-22, CXCL-1, -2, -3, -4, -5, -7, -9, -10, -11, -12, -13, -14, -15, -16, -17, CX3CL1, CXCR-2, -3, -5, -6, -7, IL5, IL17B, IL-12B, TNFS14 (Light), EGFR, Fyn, Matrix Metalloproteases (MMPs) 2, 7, 9, 19, 20, 23, and 24, CCL-2, -14, -15, CCR-4, -7, -9 and CXCR4; IL-1 and IL-36;

wherein responsiveness of the subject to the treatment is predicted when one or more of CCL-5, CCL-22, CXCL-1,-2, -3, -4, -5, -7, -9, -10, -11, -12, -13, -14, -15, -16, -17, CX3CL1, CXCR-2, -3, -5, -6, -7, IL5, IL17B, IL-12B, TNFS14 (Light), EGFR, Fyn, Matrix Metalloproteases (MMPs) 2, 7, 9, 19, 20, 23, or 24 is upregulated in the tissue and one or more of CCL-2, -14, -15, CCR-4, -7, -9, CXCR4, IL-1 or IL-36 is downregulated in the tissue.

It is to be understood that both the foregoing general description and the following detailed description are exemplary, and thus do not restrict the scope of the invention. Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The skilled artisan will understand that the drawings, described below, are for illustration purposes only. The drawings are not intended to limit the scope of the present teachings in any way.

FIG. 5. GRIM-19$^{-ve}$ signature.

FIG. 8. Open reading frame of Cell-Penetrating Peptide (CPP)-tagged AcGFP (Baculoviral expression).

FIG. 9. Open reading frame of Cell-Penetrating Peptide (CPP)-tagged human GRIM-19 (bacterial expression)

FIG. 10. Open reading frame of Myc epitope-tagged human GRIM-19 (Lentiviral vector).

DETAILED DESCRIPTION

Figure 1:
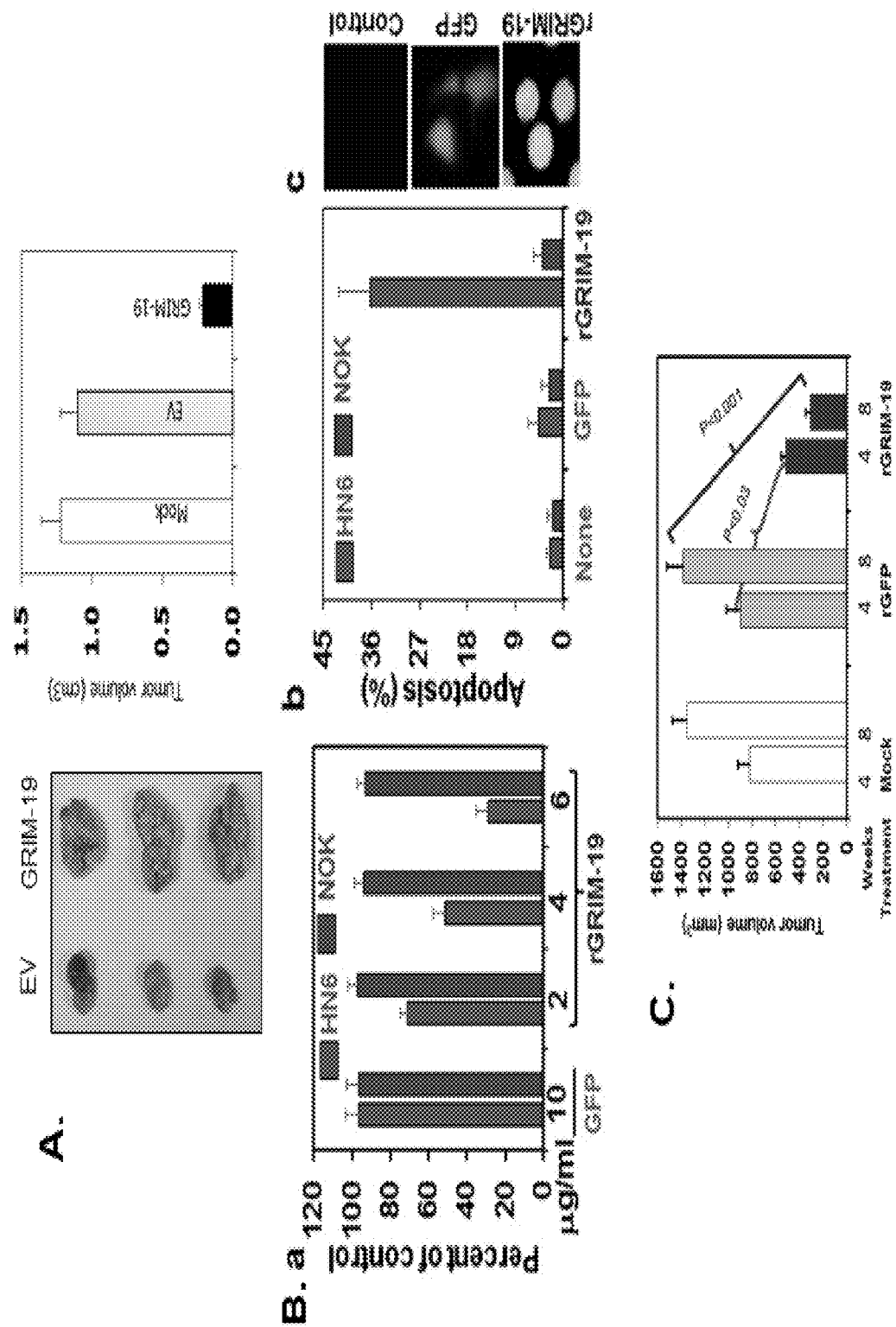
FIG. 1. A. GRIM-19 suppresses tumor growth of human cervical cells (HeLa). Mice were transplanted with HeLa on the dorsal side. 7 weeks later (when palpable tumors developed (to an average size of 0.2 cm$^3$) mice were treated with lentiviruses (10$^8$ particles on 6 different days) expressing either empty vector (EV) or GRIM-19 and tumor growth was measured. B. rGRIM-19 induces growth suppression in HN6 tumor cells but not in normal oral keratinocyte (NOK). Cells were treated with the indicated quantities of rGRIM-19. a) Growth observed in GFP or rGRIM-19 treated cells (3 days) were expressed as a percent of untreated control taken as 100%. b) Cells were assessed for signs of apoptosis using Annexin-V+ staining. (n=4/treatment) and apoptosis was measured based on our previously published protocols[10,11]. c) rGRIM-19 enters HN6 cells. FITC-anti-HA-tag antibody were used to detect rGRIM-19 after fixing the cells. Photomicrographs were captured 3 h after incubation. Such entry was found even at 30' of treatment (not shown). C. Tumor growth suppressive effects of rGRIM-19. Male athymic nude mice were transplanted subcutaneously with a GRIM-19 deficient human prostate tumor cell line PC3 (10$^6$/mouse on the dorsal side). Five weeks later (when palpable tumors developed to an average size of 580 mm$^3$) were treated with none (mock control, HBSS only) rGFP (500 µg/60 µl/mouse), rGRIM-19 (500 µg/60 µl/mouse) (5 mice/group) thrice a week for 3 weeks into the tumor and growth was measured at the indicated times.

The invention is based on the surprising discovery that administration of GRIM-19 fusion proteins or viral vectors comprising GRIM-19 is effective in the treatment of cancer. The invention is also based on the discovery of marker genes that predict responsiveness to GRIM-19 treatment.

Reference will now be made in detail to embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used).

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. Furthermore, where the description of one or more embodiments uses the term "comprising," those skilled in the art would understand that, in some specific instances, the embodiment or embodiments can be alternatively described using the language "consisting essentially of" and/or "consisting of." As used herein, the term "about" means at most plus or minus 10% of the numerical value of the number with which it is being used.

It is contemplated that any method or composition described herein can be implemented with respect to any other method or composition described herein.

One skilled in the art may refer to general reference texts for detailed descriptions of known techniques discussed herein or equivalent techniques. These texts include *Current Protocols in Molecular Biology* (Ausubel et. al., eds. John Wiley & Sons, N.Y. and supplements thereto), *Current Protocols in Immunology* (Coligan et al., eds., John Wiley St Sons, N.Y. and supplements thereto), *Current Protocols in Pharmacology* (Enna et al., eds. John Wiley & Sons, N.Y. and supplements thereto) and *Remington: The Science and Practice of Pharmacy* (Lippincott Williams & Wilicins, 2Vt edition (2005)), for example.

As further described herein, the disclosure provides engineered GRIM-19 proteins and biologically active fragments and derivatives thereof, nucleic acids encoding such proteins, vectors comprising the nucleic acids, compositions comprising the vectors, nucleic acids and/or proteins, and cells encompassing the vectors, nucleic acids, and/or proteins. The disclosure further provides methods of treating and/or preventing one or more diseases or conditions in a subject by administering effective amounts of the compositions. Further described herein are viral vectors encoding GRIM-19, biologically active fragments and derivatives thereof, and compositions thereof and methods of treatment by administering the same. Also provided are methods for predicting and/or evaluating a response to treatment using one or more markers associated with responsiveness to GRIM-19.

I. Nucleic Acids

In some embodiments, the invention provides a nucleic acid molecule encoding a fusion protein comprising
  i) a nucleotide sequence encoding GRIM-19 or a biologically active fragment or derivative thereof; and
  ii) a nucleotide sequence encoding a protein transduction domain.

In some embodiments, a nucleotide sequence encoding GRIM-19 or a biologically active fragment or derivative thereof may be derived from genomic DNA, i.e., cloned directly from the genome of a particular organism. In some embodiments, however, the nucleic acid would comprise complementary DNA (cDNA). The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression.

The organismal source of GRIM-19 is not limiting. In some embodiments, the GRIM-19 nucleic acid sequence is derived from a mammal, bird, reptile or fish. In some embodiments, the GRIM-19 is of human origin. In some embodiments, the GRIM-19 is from dog, cat, horse, mouse, rat, guinea pig, sheep, cow, pig, monkey, or ape.

The nucleic acid molecules may be produced using recombinant DNA technology (e.g., polymerase chain reaction (PCR) amplification, cloning) or chemical synthesis. GRIM-19 nucleic acids include natural nucleic acid molecules and homologues thereof, including, but not limited to, natural allelic variants and modified nucleic acid molecules in which nucleotides have been inserted, deleted, substituted, and/or inverted in such a manner that such modifications provide the desired effect (e.g., production of GRIM-19 protein in non-human expression systems).

In some embodiments, the coding sequence of GRIM-19 is encoded by SEQ ID NO:1. "GRIM-19" nucleic acid in accordance with the invention may contain a variety of different bases compared to the wild-type sequence and yet still encode a corresponding polypeptide that exhibits the biological activity of the native GRIM-19 polypeptide.

In some embodiments, a particular nucleotide sequence encoding GRIM-19 polypeptide may be identical over its entire length to the coding sequence in SEQ ID NO:1. In some embodiments, a particular nucleotide sequence encoding GRIM-19 polypeptide may be an alternate form of SEQ ID NO:1 due to degeneracy in the genetic code or variation in codon usage encoding the polypeptide of SEQ ID NO:11.

In some embodiments, the nucleic acid sequence of GRIM-19 contain a nucleotide sequence that is highly identical, at least 90% identical, with a nucleotide sequence encoding GRIM-19 polypeptide. In some embodiments, the nucleic acid sequence of GRIM-19 comprises a nucleotide sequence that is at least 60%, 65%, 70%, 75%, 80%, 85%, 90%, 91%, 92%, 93%, 94%, 95%, 96%, 97%, 98% 99% or 100% identical with the encoding nucleotide sequence set forth in SEQ ID NO:1.

When a polynucleotide of the invention is used for the recombinant production of GRIM-19 polypeptide, the polynucleotide may include the coding sequence for the full-length polypeptide or a fragment thereof, by itself; the coding sequence for the full-length polypeptide or fragment in reading frame with other coding sequences, such as those encoding a leader or secretory sequence, a pre-, or pro or prepro-protein sequence, or other fusion peptide portions. The polynucleotide may also contain non-coding 5' and 3' sequences, such as transcribed, non-translated sequences, splicing and polyadenylation signals, ribosome binding sites and sequences that stabilize mRNA.

In some embodiments, the nucleotide sequence encoding GRIM-19 or a biologically active fragment or derivative thereof includes nucleic acid molecules comprising a polynucleotide having a nucleotide sequence at least 90%, 91%, 92%, 93%, 94%, 95%, 96%, 97%, 98% 99% or 100% identical to (a) a nucleotide sequence encoding GRIM-19 having the amino acid sequence in SEQ ID NO:11; or (b) a nucleotide sequence complementary to the nucleotide sequences in (a).

Conventional means utilizing known computer programs such as the BestFit program (Wisconsin Sequence Analysis Package, Version 10 for Unix, Genetics Computer Group, University Research Park, 575 Science Drive, Madison, Wis. 53711) may be utilized to determine if a particular nucleic acid molecule is at least 90%, 91%, 92%, 93%, 94%, 95%, 96%, 97%, 98% or 99% identical to SEQ ID NO:1.

In some embodiments, the nucleotide sequence encoding GRIM-19 or a biologically active fragment or derivative thereof encode an amino acid sequence of GRIM-19 of SEQ ID NO:11, in which 1, 2, 3, 4, 5, 6, 7, 8, 9, 10 or more amino acid residues are substituted, deleted or added, in any combination.

In some embodiments, the nucleotide sequences are at least 90% identical over their entire length to a polynucleotide encoding a GRIM-19 having the amino acid sequence set out in SEQ ID NO:11, and polynucleotides which are complementary to such polynucleotides. In some embodiments, the polynucleotides are at least 91%, 92%, 93%, 94%, 95%, 96%, 97%, 98%, or at least 99% identical.

In some embodiments, the nucleic acid molecule encodes a biologically active fragment of GRIM-19 protein. In some embodiments, the biologically active fragment can be at least about 201, 210, 222, 231, 240, 252, 261, 270, 282, 291, 300, 312, 321, 330, 342, 351, 360, 372, 381, 390, 402, 405, 408, 411, 414, 417, 420, 423, 426, or 429 nucleotides in length.

In accordance with the invention, the nucleic acids encoding GRIM-19, a biologically active fragment or derivative thereof, are fused to a nucleic acid sequence encoding a protein transduction domain (PTD). PTDs are short modular motifs[49-52], which, when attached to heterologous proteins, can transfer proteins across cell membranes. These short motifs, generally rich in positively charged amino acids[50], permit transfer of proteins across plasma membrane, without requiring any receptors for their internalization[49,50]. Viral and cellular proteins—such as the HIV-TAT, herpes simplex viral VP22, the homeodomain protein antennapedia, lactoferrin and fibroblast growth factor contain such domains, which can be modularly attached to other proteins. PTDs are also called cell delivery domain or cell transduction domains.

The PTD sequence is not limiting, provided it encodes a peptide sequence that enhances uptake of a functional polypeptide by cells. In some embodiments, the PTD nucleic acid sequence comprises a nucleic acid encoding RRRRRRRRRPSASYPYDVPDYA (SEQ ID NO:3). In some embodiments, the PTD nucleic acid sequence comprises a nucleic acid encoding one or more variants of TAT protein from HIV selected from GRKKRRQRRR (SEQ ID NO: 5), YGRKKRRQRRR (SEQ ID NO: 7), or GRKKRRQ (SEQ ID NO: 9). Alternate forms of TAT can also be used. Non-limiting examples of PTDs which can be used in the present invention are shown in Table 1.

TABLE 1

Protein Transduction Domain Sequences

| PROTEIN TRANSDUCTION DOMAINS | SEQ ID NO: |
|---|---|
| RRRRRRRRRPSASYPYDVPDYA | 3 |
| GRKKRRQRRR | 5 |
| YGRKKRRQRRR | 7 |

TABLE 1-continued

Protein Transduction Domain Sequences

| PROTEIN TRANSDUCTION DOMAINS | SEQ ID NO: |
|---|---|
| GRKKRRQ | 9 |
| RQIKIWFQNRRMKWKK | 13 |
| RRMKWKK | 14 |
| RRWRRWWRRWWRRWRR | 15 |
| RGGRLSYSRRRFSTSTGR | 16 |
| RKKRRQRRR | 17 |
| YARAAARQARA | 18 |
| RRRRRRRR | 19 |
| KKKKKKKK | 20 |
| GWTLNSAGYLLGKINLKALAALAKXIL | 21 |
| SRRHHCRSKAKRSRHH | 22 |
| NRARRNRRRVR | 23 |
| RQLRIAGRRLRGRSR | 24 |
| KLIKGRTPIKFGK | 25 |
| RRIPNRRPRR | 26 |
| KLALKLALKALKAALKLA | 27 |
| KLAKLAKKLAKLAK | 28 |
| GALFLGFLGAAGSTNGAWSQPKKKRKV | 29 |
| KETWWETWWTEWSQPKKKRKV | 30 |
| LKKLLKKLLKKLLKKLLKKL | 31 |
| QAATATRGRSAASRPTERPRAPARSASRPRRPVE | 32 |
| MGLGLHLLVLAAALQGAKSKRKV | 33 |
| AAVALLPAVLLALLAPAAANYKKPKL | 34 |
| MANLGYWLLALFVTMWTDVGLCKKRPKP | 35 |
| LGTYTQDFNKFHTFPQTAIGVGAP | 36 |
| DPKGDPKGVTVTVTVTGKGDPXPD | 37 |
| PPPPPPPPPPPPPP | 38 |
| VRLPPPVRLPPPVRLPPP | 39 |
| PRPLPPPRPG | 40 |
| SVRRRPRPPYLPRPRPPPFFPPRLPPRIPP | 41 |
| TRSSRAGLQFPVGRVHRLLRK | 42 |
| GIGKFLHSAKKFGKAFVGEIMNS | 43 |
| KWKLFKKIEKVGQNIRDGIIKAGPAVAVVGQATQIAK | 44 |
| ALWMTLLKKVLKAAAKAALNAVLVGANA | 45 |
| GIGAVLKVLTTGLPALISWIKRKRQQ | 46 |
| INLKALAALAKKIL | 47 |
| GFFALIPKIISSPLPKTLLSAVGSALGGSGGQE | 48 |
| LAKWALKQGFAKLKS | 49 |

TABLE 1-continued

Protein Transduction Domain Sequences

| PROTEIN TRANSDUCTION DOMAINS | SEQ ID NO: |
|---|---|
| SMAQDIISTIGDLVKWIIQTVNXFTKK | 50 |
| LLGDFFRKSKEKIGKEFKRIVQRIKQRIKDFLANLVPRTES | 51 |
| PAWRKAFRWAWRMLKKAA | 52 |
| KLKLKLKLKLKLKLKLKL | 53 |
| LLILLRRRIRKQANAHSK | 54 |
| GALFLGWLGAAGSTMGAKKKRKV | 55 |

In some embodiments, a linker may be used to connect one or more PTDs and GRIM-19. In some embodiments, the PTD is fused or linked in frame to the N-terminal and/or C-terminal end of any one of the GRIM-19 full-length, or biologically active fragments or derivatives thereof described throughout the disclosure. In some embodiments, the GRIM-19 sequences are located downstream from the PTD sequence, i.e., the PTD sequence is N-terminal to the GRIM-19 sequence In some embodiments, the nucleic acid sequence encoding the PTD is selected from:

(SEQ ID NO: 2)
AGACGAAGGCGCAGACGGAGGCGTAGACCGTCTGCCAGCTATCCATACG
ACGTGCCTGACTACGCG, (SEQ ID NO: 4)
GGCCGTAAAAAACGCCGTCAACGCCGCCGT, (SEQ ID NO: 6)
TATGGCCGTAAAAAACGCCGTCAACGCCGCCGT
and (SEQ ID NO: 8)
GGCCGTAAAAAACGCCGTCAA.

In some embodiments, the GRIM-19 nucleic acid sequence has been optimized for expression in alternative host organisms (e.g., non-human). Although as described above, the genetic code is degenerate, so frequently one amino acid may be coded for by two or more nucleotide codons. Thus, multiple nucleic acid sequences may encode one amino acid sequence. Although this creates identical proteins, the nucleic acids themselves are distinct, and can have other distinct properties. As described herein, one aspect of the choice of codon usage can be (but is not limited to) the ability to express a protein in a non-native cells (e.g., a human protein in bacteria or yeast), or the level of expression in such cells. In order to obtain enough protein for purification, testing, and use in in vitro assays, in animal models, and eventually in clinical development, efficient protein expression in non-human systems is needed.

In some embodiments, the nucleic acid sequence further includes a nucleotide sequence encoding one or more of an epitope tag or a purification tag.

The term "epitope tag" as used herein in reference to nucleic acid molecules refers to nucleotides encoding peptide sequences that are recognized and bound by the variable region of an antibody or fragment. In some embodiments, the epitope tag is not part of the native protein. In some embodiments, the epitope tag is removable. In some embodiments, the epitope tag is not intrinsic to the protein's native biological activity. Examples of epitope tags include, but are not limited to Myc, HA and FLAG.

The term "purification tag" as used herein in reference to nucleic acid molecules refers to nucleotides encoding peptide sequences that facilitate the purification of the protein, but are generally not necessary for the protein's biological activity. In some embodiments, purification tags may be removed following protein purification. Examples of purification tags include, but are not limited to glutathione S-transferase (GST) or 6×-histidine (H6).

In some embodiments, the epitope tag is selected from Myc, HA and FLAG and combinations thereof. In some embodiments, the purification tag is one or more of glutathione-S-transferase (GST) or 6×-histidine (H6).

In some embodiments, the nucleic acid also encodes a cleavage site for a protease. In some embodiments, the cleavage site is a enterokinase target sequence, located downstream from one or more epitope and/or purification tags.

In some embodiments, the nucleic acid molecule encoding a fusion protein comprises SEQ ID NO:10.

II. Vectors, Host Cells, and Recombinant Expression

The present invention also relates to vectors that comprise the nucleic acids of the present invention, including cloning vectors and expression vectors, host cells which are genetically engineered with vectors of the invention and methods for the production of polypeptides of the invention by recombinant techniques. Cell-free translation systems can also be employed to produce such proteins using RNAs derived from the DNA constructs of the invention.

Representative examples of appropriate hosts include bacterial cells, such as streptococci, staphylococci, *Escherichia coli, Streptomyces* and *Bacillus subtilis*; fungal cells, such as yeast and *Aspergillus*; insect cells such as *Drosophila* S2 and *Spodoptera* Sf9; mammalian cells such as CHO, COS, HeLa, C127, 3T3, BHK, HEK-293 and Bowes melanoma. A great variety of expression systems can be used, including DNA or RNA vectors.

In other embodiments, this invention provides an isolated nucleic acid molecules of the invention operably linked to a heterologous promoter. The invention further provides an isolated nucleic acid molecule operably linked to a heterologous promoter, wherein said isolated nucleic acid molecule is capable of expressing a fusion protein comprising GRIM-19, or a biologically active fragment or derivative thereof when used to transform an appropriate host cell.

Methods for the production of polypeptides of the invention including culturing a host cells transfected with one or more of the vectors of the present invention under conditions promoting expression of the polypeptide encoded by the vector, and isolating the polypeptide so expressed from the cell culture.

Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MAXBAC 2.0 from INVITROGEN and BACPACK baculovirus expression system from CLONTECH.

Other examples of expression systems include COMPLETE CONTROL Inducible Mammalian Expression System from STRATAGENE, which involves a synthetic ecdysone-inducible receptor, or its pET Expression System, an *E. coli* expression system. Another example of an inducible expression system is available from INVITROGEN, which carries the T-REX (tetracycline-regulated expression) System, an inducible mammalian expression system that uses the full-length CMV promoter. INVITROGEN also provides a yeast expression system called the *Pichia methanolica* Expression System, which is designed for high-level production of recombinant proteins in the methylotrophic yeast *P. methanolica*. One of skill in the art would know how to manipulate a vector, such as an expression construct, to produce a nucleic acid sequence or its cognate polypeptide, protein, or peptide.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented.

One embodiment involves the use of gene transfer to immortalize cells for the production of proteins. The nucleic acid for the protein of interest may be transferred as described above into appropriate host cells followed by culture of cells under the appropriate conditions.

Examples of useful mammalian host cell lines are Vero and HeLa cells and cell lines of Chinese hamster ovary, W138, BHK, COS-7, HEK-293, HepG2, NIH3T3, RIN and MDCK cells. In addition, a host cell clone may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to methotrexate; gpt, that confers resistance to mycophenolic acid; neo, that confers resistance to the aminoglycoside G418; and hygro, that confers resistance to hygromycin.

As used herein, the terms "cell," "cell line," and "cell culture" may be used interchangeably. All of these terms also include their progeny, which are any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes (e.g., bacteria or yeast), depending upon whether the desired result is replication of the vector or expression of part or all of the vector-encoded nucleic acid sequences. Numerous cell lines and cultures are available for use as a host cell, and they can be obtained through the American Type Culture Collection (ATCC). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KCB, as well as a number of commercially available bacterial hosts such as SURE Competent Cells and SOLOPACK Gold Cells (STRATAGENE, La Jolla). Alternatively, bacterial cells such as *E. coli* LE392 could be used as host cells for phage viruses.

Examples of eukaryotic host cells for replication and/or expression of a vector include HeLa, NIH3T3, Jurkat, HEK-293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

III. Viral Vectors/Gene Delivery Systems

In some embodiments, the invention provides a viral vector encoding GRIM-19 or a biologically active fragment or derivative thereof. In some embodiments, the viral vector comprises a nucleic acid sequence encoding GRIM-19 or a biologically active fragment or derivative thereof as provided herein. In some embodiments, the GRIM-19 or the biologically active fragment or derivative thereof is fused to an epitope tag. The epitope tag is not limiting, and in some embodiments is selected from the group consisting of Myc, FLAG, hemagglutinin (HA) and/or combinations thereof. In some embodiments, the GRIM-19 or a biologically active fragment or derivative thereof encodes a protein that is at least 90% identical to SEQ ID NO:11.

The viral vector is not limiting. In some embodiments, the viral vector will typically comprise a highly attenuated, non-replicative virus. Viral vectors include, but are not limited to, DNA viral vectors such as those based on adenoviruses, herpes simplex virus, avian viruses, such as Newcastle disease virus, poxviruses such as vaccinia virus, and parvoviruses, including adeno-associated virus; and RNA viral vectors, including, but not limited to, the retroviral vectors. Vaccinia vectors and methods useful in immunization protocols are described in U.S. Pat. No. 4,722,848. Retroviral vectors include murine leukemia virus, and lentiviruses such as human immunodeficiency virus. Naldini et al. (1996) *Science* 272:263-267. Replication-defective retroviral vectors harboring a nucleotide sequence of interest as part of the retroviral genome can be used. Such vectors have been described in detail. (Miller et al. (1990) *Mol. Cell. Biol.* 10:4239; Kolberg, R. (1992) *J. NIH Res.* 4:43; Cornetta et al. (1991) *Hum. Gene Therapy* 2:215).

Adenovirus and adeno-associated virus vectors useful in the invention may be produced according to methods already taught in the art. (See, e.g., Karlsson et al. (1986) EMBO 5:2377; Carter (1992) *Current Opinion in Biotechnology* 3:533-539; Muzcyzka (1992) *Current Top. Microbiol. Immunol.* 158:97-129; *Gene Targeting: A Practical Approach* (1992) ed. A. L. Joyner, Oxford University Press, NY). Several different approaches are feasible.

Alpha virus vectors, such as Venezuelan Equine Encephalitis (VEE) virus, Semliki Forest virus (SFV) and Sindbis virus vectors, can be used for efficient gene delivery. Replication-deficient vectors are available. Such vectors can be administered through any of a variety of means known in the art, such as, for example, intranasally or intratumorally. See Lundstrom, *Curr. Gene Ther.* 2001 1:19-29.

Additional literature describing viral vectors which could be used in the methods of the present invention include the following: Horwitz, M. S., *Adenoviridae and Their Replication*, in Fields, B., et al. (eds.) *Virology*, Vol. 2, Raven Press New York, pp. 1679-1721, 1990); Graham, F. et al., pp. 109-128 in *Methods in Molecular Biology*, Vol. 7: *Gene Transfer and Expression Protocols*, Murray, E. (ed.), Humana Press, Clifton, N.J. (1991); Miller, et al. (1995) *FASEB Journal* 9:190-199, Schreier (1994) *Pharmaceutica Acta Helvetiae* 68:145-159; Schneider and French (1993) *Circulation* 88:1937-1942; Curiel, et al. (1992) *Human Gene Therapy* 3:147-154; WO 95/00655; WO 95/16772; WO 95/23867; WO 94/26914; WO 95/02697 (Jan. 26, 1995); and WO 95/25071.

In some embodiments, the viral vector is a retrovirus/lentivirus, adenovirus, adeno-associated virus, alpha virus, vaccinia virus or a herpes simplex virus. In some embodiments, the viral vector is a lentiviral vector comprising the nucleotide sequence of SEQ ID NO:56, which encodes GRIM-19 fused to a Myc epitope (SEQ ID NO:57).

IV. Proteins

In another embodiment, the invention provides a fusion protein comprising
  i) GRIM-19 or a biologically active fragment or derivative thereof; and
  ii) a protein transduction domain.

The terms "polypeptide," "peptide," and "protein" are used interchangeably herein to refer to a polymer of amino acid residues. The terms apply to naturally occurring amino acid polymers as well as amino acid polymers in which one or more amino acid residues is a non-naturally occurring amino acid, for example, an amino acid analog. As used herein, the terms encompass amino acid chains of any length, including full length proteins, wherein the amino acid residues are linked by covalent peptide bonds.

In some embodiments, the amino acid sequence of GRIM-19 comprises SEQ ID NO: 11. In some embodiments, the fusion protein comprises biologically active fragment or derivatives of GRIM-19. In some embodiments, the biologically active fragment or derivatives of GRIM-19 have at least 90% identity to SEQ ID NO:11. In some embodiments, the GRIM-19 or a biologically active fragment or derivative thereof has at least 91%, 92%, 93%, 94%, 95%, 96%, 97%, 98% or 99% identity to the polypeptide of SEQ ID NO:11.

In some embodiments, the fusion protein comprises a biologically active fragment of GRIM-19. A fragment is a polypeptide having an amino acid sequence that entirely is the same as part but not all of the amino acid sequence of the aforementioned GRIM-19 polypeptide. In some embodiments, a fragment may constitute at least about 30 contiguous amino acids identified in SEQ ID NO:11. In some embodiments, the fragment is at least about 30, 35, 40, 45, 50, 55, 60, 65, 70, 75, 80, 85, 90, 95, 100, 105, 110, 115, 120, 121, 122, 123, 124, 125, 126, 127, 128, 129, 130, 131, 132, 133, 134, 135, 136, 137, 138, 139, 140, 141, 142, or 143 contiguous amino acids identified in SEQ ID NO:11.

In some embodiments the fragments include, for example, truncation polypeptides having the amino acid sequence of GRIM-19, except for deletion of a continuous series of residues that includes the amino terminus, or a continuous series of residues that includes the carboxyl terminus or deletion of two continuous series of residues, one including the amino terminus and one including the carboxyl terminus. In some embodiments, fragments are characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, high antigenic index regions, or functional domains. Biologically active fragments are those that mediate protein activity, including those with a similar activity or an improved activity, or with a decreased undesirable activity.

In one embodiment, the fragment comprises the final 30, 35, 40, 45, 50, 55, 60, 65, 70, 75, 80, 85, 90, 95, 100, 105, 110, 115, 120, 121, 122, 123, 124, 125, 126, 127, 128, 129, 130, 131, 132, 133, 134, 135, 136, 137, 138, 139, 140, 141, 142, or 143 amino acids of GRIM-19 of SEQ ID NO:11.

In one embodiment, the fragment comprises the first 30, 35, 40, 45, 50, 55, 60, 65, 70, 75, 80, 85, 90, 95, 100, 105, 110, 115, 120, 121, 122, 123, 124, 125, 126, 127, 128, 129, 130, 131, 132, 133, 134, 135, 136, 137, 138, 139, 140, 141, 142, or 143 amino acids of GRIM-19 of SEQ ID NO:11.

Biologically active fragments or derivatives of GRIM-19 include polypeptides having an amino acid sequence at least 90% identical to that of SEQ ID NO:11 or fragments thereof with at least 90% identity to the corresponding fragment of SEQ ID NO:11, all of which retain the biological activity of GRIM-19. Included in this group are derivatives of the defined sequence and fragment. In some embodiments, the derivatives are those that vary from the reference by conservative amino acid substitutions, i.e., those that substitute a residue with another of like characteristics. Typical substitutions are among Ala, Val, Leu and Ile; among Ser and Thr; among the acidic residues Asp and Glu; among Asn and Gln; and among the basic residues Lys and Arg, or aromatic residues Phe and Tyr. In some embodiments, the polypeptides are derivatives in which 1, 2, 3, 4, 5, 6, 7, 8, 9, 10 or more amino acids are substituted, deleted, or added in any combination.

The fusion proteins comprising GRIM-19 and biologically active fragments or derivatives thereof can be prepared in any suitable manner. Such polypeptides include recombinantly produced polypeptides, synthetically produced polypeptides, or polypeptides produced by a combination of these methods. Means for preparing such polypeptides are well understood in the art.

In accordance with the invention, the fusion protein comprising GRIM-19, a biologically active fragment or derivative thereof, further comprises a protein transduction domain (PTD) to facilitate uptake of the encoded polypeptide by cells, thereby facilitating the polypeptide's therapeutic activity when administered to a subject. The PTD is not limiting and is described above. In some embodiments, the PTD sequence comprises SEQ ID NOS:3, 5, 7, 9 or 13-55.

In some embodiments, the fusion protein further comprises one or more epitope tags and/or purification tags. The epitope tag is not limiting and can include a Myc tag, a FLAG tag, a hemagglutinin (HA) tag and/or combinations thereof. The purification tag is not limiting and can include a histidine tag (6×), a glutathione S-Transferase tag or a combination thereof.

In some embodiments, the fusion protein comprises an enzymatic cleavage site to further aid in purification and processing of the fusion protein. In some embodiments, the cleavage site is an enterokinase cleavage site.

In some embodiments, the fusion protein comprises a histidine tag (6×), a FLAG tag, a hemagglutinin (HA) tag, an enterokinase cleavage site and SEQ ID NO:3 as the PTD. In some embodiments, the fusion protein comprises SEQ ID NO:12.

V. Pharmaceutical Compositions

Where clinical applications are contemplated, it will be necessary to prepare pharmaceutical compositions in a form appropriate for the intended application. Generally, this will entail preparing compositions that are suitable for administration to a subject, e.g., essentially free of pyrogens, as well as other impurities that could be harmful to humans or animals.

In some embodiments, the invention provides a pharmaceutical composition comprising a fusion protein comprising a protein transduction domain and GRIM-19 or a biologically active fragment or derivative thereof as described herein.

In some embodiments, the invention provides a pharmaceutical composition comprising a viral vector encoding GRIM-19 or a biologically active fragment or derivative thereof as described herein.

In some embodiments, the compositions are pharmaceutical compositions comprising effective amounts of fusion proteins or viral vectors which are capable of treating of one or more diseases or conditions described herein.

In some embodiments, the composition comprises appropriate salts and/or buffers to render delivery vectors or fusion proteins stable and allow for uptake by target cells. In some embodiments, compositions comprising a viral vector or fusion protein is dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. Except insofar as any conventional media or agent is incompatible with the vectors fusion proteins of the present technology, its use in therapeutic compositions is contemplated. Supplementary active ingredients also can be incorporated into the compositions.

The active compositions of the present technology may include classic pharmaceutical preparations. Administration of these compositions according to the present technology will be via any common route so long as the target tissue is available via that route. Such routes of administration may include oral, parenteral (including intravenous, intramuscular, subcutaneous, intradermal, intra-articular, intra-synovial, intrathecal, intra-arterial, intracardiac, subcutaneous, intraorbital, intracapsular, intraspinal, intrasternal, and transdermal), nasal, buccal, urethral, rectal, vaginal, mucosal, dermal, or topical (including dermal, buccal, and sublingual). Alternatively, administration may be by orthotopic, intradermal, subcutaneous, intramuscular, intraperitoneal or intravenous injection. Such compositions would normally be administered as pharmaceutically acceptable compositions. Of particular interest is direct intratumoral administration, perfusion of a tumor, or administration local or regional to a tumor, for example, in the local or regional vasculature or lymphatic system, or in a resected tumor bed. Administration can also be via nasal spray, surgical implant, internal surgical paint, infusion pump, or via catheter, stent, balloon or other delivery device. The most useful and/or beneficial mode of administration can vary, especially depending upon the condition of the recipient and the disorder being treated.

In some embodiments, compositions which are dispersions can also be prepared, e.g., in glycerol, liquid polyethylene glycols, and mixtures thereof and in oils. Under ordinary conditions of storage and use, these preparations may contain a preservative to prevent the growth of microorganisms.

In some embodiments, pharmaceutical forms suitable for injectable use include sterile aqueous solutions or dispersions and sterile powders for the extemporaneous preparation of sterile injectable solutions or dispersions. In all cases, the form must be sterile and should be fluid to the extent that easy syringability exists. In some embodiments, it must be stable under the conditions of manufacture and storage and must be preserved against the contaminating action of microorganisms, such as bacteria and fungi. In some embodiments, the carrier can be a solvent or dispersion medium containing, for example, water, ethanol, polyol (e.g., glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In some embodiments, it will be preferable to include isotonic agents, for example, sugars or sodium chloride. Prolonged absorption of the injectable compositions can be brought about by the use in the compositions of agents delaying absorption, for example, aluminum monostearate and gelatin.

In some embodiments, sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions can be administered in a variety of dosage forms. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA Office of Biologics standards.

For oral administration the polypeptides of the present technology may be incorporated with excipients and used in the form of non-ingestible mouthwashes and dentifrices. It is anticipated that virtually any pill or capsule type known to one of skill in the art including, e.g., coated, and time delay, slow release, etc., may be used with the present technology. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, creams, powders and slurries. The active ingredient may be added in a therapeutically effective amount to a paste dentifrice that may include water, binders, abrasives, flavoring agents, foaming agents, and humectants.

Pharmaceutical compositions suitable for oral dosage may take various forms, such as tablets, capsules, caplets, and wafers (including rapidly dissolving or effervescing), each containing a predetermined amount of the active agent. The compositions may also be in the form of a powder or granules, a solution or suspension in an aqueous or non-aqueous liquid, and as a liquid emulsion (oil-in-water and water-in-oil). The active agents may also be delivered as a bolus, electuary, or paste. It is generally understood that methods of preparations of the above dosage forms are generally known in the art, and any such method would be suitable for the preparation of the respective dosage forms for use in delivery of the compositions.

In one embodiment, compositions may be administered orally in combination with a pharmaceutically acceptable vehicle such as an inert diluent or an edible carrier. Oral compositions may be enclosed in hard or soft shell gelatin capsules, may be compressed into tablets or may be incorporated directly with the food of the patient's diet. The percentage of the composition and preparations may be varied; however, the amount of substance in such therapeutically useful compositions is preferably such that an effective dosage level will be obtained.

Hard capsules containing the compositions may be made using a physiologically degradable composition, such as gelatin. Such hard capsules comprise the compound, and may further comprise additional ingredients including, for example, an inert solid diluent such as calcium carbonate, calcium phosphate, or kaolin. Soft gelatin capsules containing the compound may be made using a physiologically degradable composition, such as gelatin. Such soft capsules comprise the compound, which may be mixed with water or an oil medium such as peanut oil, liquid paraffin, or olive oil.

Sublingual tablets are designed to dissolve very rapidly. Examples of such compositions include ergotamine tartrate, isosorbide dinitrate, and isoproterenol HCL. The compositions of these tablets contain, in addition to the drug, various soluble excipients, such as lactose, powdered sucrose, dextrose, and mannitol. The solid dosage forms of the present technology may optionally be coated, and examples of suitable coating materials include, but are not limited to, cellulose polymers (such as cellulose acetate phthalate, hydroxypropyl cellulose, hydroxypropyl methylcellulose, hydroxypropyl methylcellulose phthalate, and hydroxypropyl methylcellulose acetate succinate), polyvinyl acetate phthalate, acrylic acid polymers and copolymers, and methacrylic resins (such as those commercially available under the trade name EUDRAGIT), zein, shellac, and polysaccharides.

Powdered and granular compositions of a pharmaceutical preparation may be prepared using known methods. Such compositions may be administered directly to a patient or used in the preparation of further dosage forms, such as to form tablets, fill capsules, or prepare an aqueous or oily suspension or solution by addition of an aqueous or oily vehicle thereto. Each of these compositions may further comprise one or more additives, such as dispersing or wetting agents, suspending agents, and preservatives. Additional excipients (e.g., fillers, sweeteners, flavoring, or coloring agents) may also be included in these compositions.

Liquid compositions of pharmaceutical compositions which are suitable for oral administration may be prepared, packaged, and sold either in liquid form or in the form of a dry product intended for reconstitution with water or another suitable vehicle prior to use.

A tablet containing one or more active agent compounds described herein may be manufactured by any standard process readily known to one of skill in the art, such as, for example, by compression or molding, optionally with one or more adjuvant or accessory ingredient. The tablets may optionally be coated or scored and may be formulated so as to provide slow or controlled release of the active agents.

Solid dosage forms may be formulated so as to provide a delayed release of the active agents, such as by application of a coating. Delayed release coatings are known in the art, and dosage forms containing such may be prepared by any known suitable method. Such methods generally include that, after preparation of the solid dosage form (e.g., a tablet or caplet), a delayed release coating composition is applied. Application can be by methods, such as airless spraying, fluidized bed coating, use of a coating pan, or the like. Materials for use as a delayed release coating can be polymeric in nature, such as cellulosic material (e.g., cellulose butyrate phthalate, hydroxypropyl methylcellulose phthalate, and carboxymethyl ethylcellulose), and polymers and copolymers of acrylic acid, methacrylic acid, and esters thereof.

Solid dosage forms according to the present technology may also be sustained release (i.e., releasing the active agents over a prolonged period of time), and may or may not also be delayed release. Sustained release compositions are known in the art and are generally prepared by dispersing a drug within a matrix of a gradually degradable or hydrolyzable material, such as an insoluble plastic, a hydrophilic polymer, or a fatty compound. Alternatively, a solid dosage form may be coated with such a material.

Compositions for parenteral administration include aqueous and non-aqueous sterile injection solutions, which may further contain additional agents, such as antioxidants, buffers, bacteriostats, and solutes, which render the compositions isotonic with the blood of the intended recipient. The compositions may include aqueous and non-aqueous sterile suspensions, which contain suspending agents and thickening agents. Such compositions for parenteral administration may be presented in unit-dose or multi-dose containers, such as, for example, sealed ampoules and vials, and may be stores in a freeze-dried (lyophilized) condition requiring only the addition of the sterile liquid carrier, for example, water (for injection), immediately prior to use. Extemporaneous injection solutions and suspensions may be prepared from sterile powders, granules, and tablets of the kind previously described.

Compositions for rectal delivery include rectal suppositories, creams, ointments, and liquids. Suppositories may be presented as the active agents in combination with a carrier generally known in the art, such as polyethylene glycol. Such dosage forms may be designed to disintegrate rapidly or over an extended period of time, and the time to complete disintegration can range from a short time, such as about 10 minutes, to an extended period of time, such as about 6 hours.

Topical compositions may be in any form suitable and readily known in the art for delivery of active agents to the body surface, including dermally, buccally, and sublingually. Typical examples of topical compositions include ointments, creams, gels, pastes, and solutions. Compositions for administration in the mouth include lozenges.

In accordance with these embodiments, oral (topical, mucosal, and/or dermal) delivery materials can also include creams, salves, ointments, patches, liposomes, nanoparticles, microparticles, timed-release formulations and other materials known in the art for delivery to the oral cavity, mucosa, and/or to the skin of a subject for treatment and/or prevention of a condition disclosed herein. Certain embodiments concern the use of a biodegradable oral (topical, mucosal, and/or dermal) patch delivery system or gelatinous material. These compositions can be a liquid formulation or a pharmaceutically acceptable delivery system treated with a formulation of these compositions, and may also include activator/inducers.

The compositions for use in the methods of the present technology may also be administered transdermally, wherein the active agents are incorporated into a laminated structure (generally referred to as a "patch") that is adapted to remain in intimate contact with the epidermis of the recipient for a prolonged period of time. Typically, such patches are available as single layer "drug-in-adhesive" patches or as multi-layer patches where the active agents are contained in a layer separate from the adhesive layer. Both types of patches also generally contain a backing layer and a liner that is removed prior to attachment to the recipient's skin. Transdermal drug delivery patches may also be comprised of a reservoir underlying the backing layer that is separated from the skin of the recipient by a semi-permeable membrane and adhesive layer. Transdermal drug delivery may occur through passive diffusion, electrotransport, or iontophoresis.

In certain embodiments, a patch contemplated herein may be a slowly dissolving or a time-released patch. In accordance with these embodiments, a slowly dissolving patch can be an alginate patch. In certain examples, a patch may contain a detectible indicator dye or agent such as a fluorescent agent. In other embodiments, a tag (e.g., detectible tag such as a biotin or fluorescently tagged agent) can be associated with a treatment molecule in order to detect the molecule after delivery to the subject. In certain embodiments, one or more oral delivery patches or other treatment contemplated herein may be administered to a subject three times daily, twice daily, once a day, every other day, weekly, and the like, depending on the need of the subject as assessed by a health professional. Patches contemplated herein may be oral-biodegradable patches or patches for exterior use that may or may not degrade. Patches contemplated herein may be 1 mm, 2 mm, 3 mm, 4 mm to 5 mm in size or more depending on need. In treating psoriasis and chronic wounds, GRIM-19 can be delivered topically using vehicles such as glycerol, carboxymethycellulose. It can also use transdermal system (e.g., commercially available from 3M) for delivery. Subcutaneous injection into the lesion (in normal saline or PBS) can also be used.

In some embodiments, compositions may include short-term, rapid-onset, rapid-offset, controlled release, sustained release, delayed release, and pulsatile release compositions, providing the compositions achieve administration of the fusion proteins or viral vectors as described herein. See Remington's Pharmaceutical Sciences (18th ed.; Mack Publishing Company, Eaton, Pa., 1990), herein incorporated by reference in its entirety.

In certain embodiments, the compositions disclosed herein can be delivered via a medical device. Such delivery can generally be via any insertable or implantable medical device, including, but not limited to stents, catheters, balloon catheters, shunts, or coils. In one embodiment, the present technology provides medical devices, such as stents, the surface of which is coated with a compound or composition as described herein. The medical device of this technology can be used, for example, in any application for treating, preventing, or otherwise affecting the course of a disease or condition, such as those disclosed herein.

VI. Methods

In another embodiment, the invention provides a method of treating cancer comprising administering to a subject in need thereof an effective amount of a fusion protein of the invention.

In another embodiment, the invention provides a method of treating cancer comprising administering to a subject in need thereof an effective amount of a viral vector of the invention.

In another embodiment, the invention provides a method of treating an autoimmune disease comprising administering to a subject in need thereof an effective amount of a fusion protein of the invention. In some embodiments, the autoimmune disease is selected from the group consisting of ulcerative colitis, Crohn's disease, inflammatory bowel disease, rheumatoid arthritis, Sjogren's syndrome, multiple sclerosis, lupus (SLE), psoriasis, Graves' disease, and Hashimoto's thyroiditis. In some embodiments, the autoimmune disease is rheumatoid arthritis.

In another embodiment, the invention provides a method of treating an autimmune disease comprising administering to a subject in need thereof an effective amount of a viral vector of the invention. In some embodiments, the autoimmune disease is selected from the group consisting of ulcerative colitis, Crohn's disease, inflammatory bowel disease, rheumatoid arthritis, Sjogren's syndrome, multiple sclerosis, lupus (SLE), psoriasis, Graves' disease, and Hashimoto's thyroiditis. In some embodiments, the autimmune disease is rheumatoid arthritis.

As used herein, "treat" and all its forms and tenses (including, for example, treating, treated, and treatment) refers to therapeutic and prophylactic treatment. In certain aspects of the invention, those in need of treatment include those already with a pathological disease or condition of the invention (including, for example, a cancer), in which case treating refers to administering to a subject (including, for example, a human or other mammal in need of treatment) a therapeutically effective amount of a composition so that the subject has an improvement in a sign or symptom of a pathological condition of the invention. The improvement may be any observable or measurable improvement. Thus, one of skill in the art realizes that a treatment may improve the patient's condition, but may not be a complete cure of the disease or pathological condition.

In accordance with the invention, a "therapeutically effective amount" or "effective amount" is administered to the subject. As used herein a "therapeutically effective amount" or "effective amount" is an amount sufficient to decrease, suppress, or ameliorate one or more symptoms associated with the disease or condition.

The subject to be treated herein is not limiting. In some embodiments, the subject to be treated is a mammal, bird, reptile or fish. Mammals that can be treated in accordance with the invention, include, but are not limited to, humans, dogs, cats, horses, mice, rats, guinea pigs, sheep, cows, pigs, monkeys, apes and the like. The term "patient" and "subject" are used interchangeably. In some embodiments, the subject is a human.

The therapeutic agent can be administered one time or more than one time, for example, more than once per day, daily, weekly, monthly, or annually. The duration of treatment is not limiting. The duration of administration of the therapeutic agent can vary for each individual to be treated/administered depending on the individual cases and the diseases or conditions to be treated. In some embodiments, the therapeutic agent can be administered continuously for a period of several days, weeks, months, or years of treatment or can be intermittently administered where the individual is administered the therapeutic agent for a period of time, followed by a period of time where they are not treated, and then a period of time where treatment resumes as needed to treat the disease or condition. For example, in some embodiments, the individual to be treated is administered the therapeutic agent of the invention daily, every other day, every three days, every four days, 2 days per week 3 days per week, 4 days per week, 5 days per week or 7 days per week. In some embodiments, the individual is administered the therapeutic agent for 1 week, 2 weeks, 3 weeks, 4 weeks, 1 month, 2 months, 3 months, 4 months, 5 months, 6 months, 7 months, 8 months, 9 months, 10 months, 11 months, 1 year or longer.

As used herein, "cancer" refers to a pathophysiological condition whereby cells are characterized by dysregulated and/or proliferative cellular growth and the ability to induce said growth, which includes but is not limited to, carcinomas and sarcomas, such as, for example, acute lymphoblastic leukemia, acute myeloid leukemia, adrenocortical cancer, AIDS-related cancers, AIDS-related lymphoma, anal cancer, astrocytoma (including, for example, cerebellar and cerebral), basal cell carcinoma, bile duct cancer, bladder cancer, bone cancer, brain stem glioma, brain tumor (including, for example, ependymoma, meduUoblastoma, supratentorial primitive neuroectodermal, visual pathway and hypothalamic glioma), cerebral astrocytoma/malignant glioma, breast cancer, bronchial adenomas/carcinoids, Burkitt's lymphoma, carcinoid tumor (including, for example, gastrointestinal), carcinoma of unknown primary site, central nervous system lymphoma, cervical cancer, chronic lymphocytic leukemia, chronic myelogenous leukemia, chronic myeloproliferative disorders, colon cancer, colorectal cancer, cutaneous T-Cell lymphoma, endometrial cancer, ependymoma, esophageal cancer, Ewing's Family of tumors, extrahepatic bile duct cancer, eye cancer (including, for example, intraocular melanoma, retinoblastoma, gallbladder cancer, gastric cancer, gastrointestinal carcinoid tumor, gastrointestinal stromal tumor (GIST), germ cell tumor (including, for example, extracranial, extragonadal, ovarian), gestational trophoblastic tumor, glioma, hairy cell leukemia, head and neck cancer, squamous cell head and neck cancer, hepatocellular cancer, Hodgkin's lymphoma, hypopharyngeal cancer, islet cell carcinoma (including, for example, endocrine pancreas), Kaposi's sarcoma, laryngeal cancer, leukemia, lip cancer, liver cancer, lung cancer (including, for example, non-small cell), lymphoma, macroglobulinemia, malignant fibrous histiocytoma of bone/osteosarcoma, meduUoblastoma, melanoma, Merkel cell carcinoma, mesothelioma, metastatic squamous neck cancer with occult primary, mouth cancer, multiple endocrine neoplasia syndrome, multiple myeloma/plasma cell neoplasm, mycosis fungoides, myelodysplasia syndromes, myelodysplastic/myeloproliferative diseases, myeloma, nasal cavity and paranasal sinus cancer, nasopharyngeal cancer, neuroblastoma, non-Hodgkin's lymphoma, oral cancer, osteosarcoma, oropharyngeal cancer, ovarian cancer (including, for example, ovarian epithelial cancer, germ cell tumor), ovarian low malignant potential tumor, pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, pregnancy and breast cancer, primary central nervous system lymphoma, prostate cancer, rectal cancer, retinoblastoma, rhabdomyosarcoma, salivary gland cancer, soft tissue sarcoma, uterine sarcoma, Sezary syndrome, skin cancer (including, for example, non-melanoma or melanoma), small intestine cancer, supratentorial primitive neuroectodermal tumors, T-Cell lymphoma, testicular cancer, throat cancer, thymoma, thymoma and thymic carcinoma, thyroid cancer, transitional cell cancer of the renal pelvis and ureter, trophoblastic tumor (including, for example, gestational), unusual cancers of childhood and adulthood, urethral cancer, endometrial uterine cancer, uterine sarcoma, vaginal cancer, viral induced cancers (including, for example, HPV induced cancer), vulvar cancer, Waldenstrom's macroglobulinemia, Wilms' Tumor, and women's cancers.

In some embodiments, the administration of the fusion proteins or viral vectors decrease the levels of CXCL3 in the tissue of the subject. In some embodiments, the levels of CXCL3 decrease by about 10%, about 20%, about 30%, about 40%, about 50%, about 60%, about 70%, about 80%, about 90%, or about 100% over untreated levels.

In some embodiments, the administration of the fusion proteins or viral vectors decrease the levels of CXCL10 in the tissue of the subject. In some embodiments, the levels of CXCL10 decrease by about 10%, about 20%, about 30%, about 40%, about 50%, about 60%, about 70%, about 80%, about 90%, or about 100% over untreated levels.

In some embodiments, the administration of the fusion proteins or viral vectors decrease the levels of CXCR3 in the tissue of the subject. In some embodiments, the levels of CXCR3 decrease by about 10%, about 20%, about 30%, about 40%, about 50%, about 60%, about 70%, about 80%, about 90%, or about 100% over untreated levels.

In some embodiments, the administration of the fusion proteins or viral vectors decrease the levels of CCND1 in the tissue of the subject. In some embodiments, the levels of CCND1 decrease by about 10%, about 20%, about 30%, about 40%, about 50%, about 60%, about 70%, about 80%, about 90%, or about 100% over untreated levels.

In some embodiments, the subject is administered one or more additional therapeutic agents. In some embodiments, the one or more additional therapeutic agents are those commonly used to treat cancer or an autoimmune disease such as rheumatoid arthritis.

In some embodiments, the subject is administered an effective amount of a combination of viral vector of the invention, fusion protein of the invention and another agent to treat an autoimmune disease such as rheumatoid arthritis. In some embodiments, the subject is administered in combination an anti-inflammatory drug. In some embodiments, the anti-inflammatory drug is a non-steroidal anti-inflammatory drug (NSAID). In some embodiments, anti-inflammatory drug is selected from the group consisting of Antazoline, Balsalazide, Beclometasone, Betamethasone, Budesonide, Celecoxib, Colchicine, Deflazacort, Dexamethasone, Dexibuprofen, Diclofenac, Etanercept, Etodolac, Felbinac, Fenoprofen, Flumetasone, Fluorometholone, Flurbiprofen, Flurbiprofen, Fluticasone, Gentamicin, Hydrocortisone, Ibuprofen, Indometacin, Ketoprofen, Loteprednol, Mefenamic acid, Meloxicam, Mesalazine, Methylprednisolone, Mometasone, Nabumetone, Naproxen, Nepafenac, Olsalazine, Prednisolone, Rimexolone, Sulfasalazine, Sulindac, Tenoxicam, Tiaprofenic acid, Triamcinolone and combinations thereof.

In some embodiments, the subject is administered one or more anti-cancer agents and/or radiotherapy in combination with the viral vector or fusion protein to treat cancer in the subject.

In some embodiments, the subject is administered an effective amount of a combination of viral vector and fusion protein of the invention.

In some embodiments, the subject is administered an effective amount of a combination of viral vector of the invention, fusion protein of the invention and ant-cancer agent.

In some embodiments, the anti-cancer agent is selected from the group consisting of Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Adrucil (Fluorouracil), Afatinib Dimaleate, Afinitor (Everolimus), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase Erwinia chrysanthemi, Avastin (Bevacizumab), Axitinib, Azacitidine, BEACOPP, Becenum (Carmustine), Beleodaq (Belinostat), Belinostat, Bendamustine Hydrochloride, BEP, Bevacizumab, Bexarotene, Bexxar (Tositumomab and I 131 Iodine Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Busulfan, Busulfex (Busulfan), Cabazitaxel, Cabozantinib-S-Malate, CAF, Campath (Alemtuzumab), Camptosar (Irinotecan Hydrochloride), Capecitabine, CAPOX, Carboplatin, CARBOPLATIN-TAXOL, Carfilzomib, Carmubris (Carmustine), Carmustine, Carmustine Implant, Casodex (Bicalutamide), CeeNU (Lomustine) Ceritinib, Cerubidine (Daunorubicin Hydrochloride), Cervarix (Recombinant HPV Bivalent Vaccine), Cetuximab, Chlorambucil, CHLORAMBUCIL-PREDNISONE, CHOP, Cisplatin, Clafen (Cyclophosphamide), Clofarabine, Clofarex (Clofarabine), Clolar (Clofarabine), CMF, Cometriq (Cabozantinib-S-Malate), COPP, COPP-ABV, Cosmegen (Dactinomycin), Crizotinib, CVP, Cyclophosphamide, Cyfos (Ifosfamide), Cyramza (Ramucirumab), Cytarabine, Cytarabine, Liposomal, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Denosumab, DepoCyt (Liposomal Cytarabine), DepoFoam (Liposomal Cytarabine), Dexrazoxane Hydrochloride, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase Erwinia chrysanthemi), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Ifex (Ifosfamide), Ifosfamide, Ifosfamidum (Ifosfamide), Imatinib Mesylate, Imbruvica (Ibrutinib), Imiquimod, Inlyta (Axitinib), Intron A (Recombinant Interferon Alfa-2b), Iodine$^{131}$ Tositumomab and Tositumomab, Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Keytruda (Pembrolizumab), Kyprolis (Carfilzomib), Lanreotide Acetate, Lapatinib Ditosylate, Lenalidomide, Lenvatinib Mesylate, Lenvima (Lenvatinib Mesylate), Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Lynparza (Olaparib), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Neupogen (Filgrastim), Nexavar (Sorafenib Tosylate), Nilotinib, Nivolumab, Nolvadex (Tamoxifen Citrate), Nplate (Romiplostim), Obinutuzumab, OEPA, Ofatumumab, OFF, Olaparib, Omacetaxine Mepesuccinate, Oncaspar (Pegaspargase), Ontak (Denileukin Diftitox), Opdivo (Nivolumab), OPPA, Oxaliplatin, Paclitaxel, Paclitaxel Albumin-stabilized Nanoparticle Formulation, PAD, Palbociclib, Palifermin, Palonosetron Hydrochloride, Pamidronate Disodium, Panitumumab, Paraplat (Carboplatin), Paraplatin (Carboplatin), Pazopanib Hydrochloride, Pegaspargase, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, R-EPOCH, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Siltuximab, Sipuleucel-T, Somatuline Depot (Lanreotide Acetate), Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synovir (Thalidomide), Synribo (Omacetaxine Mepesuccinate), TAC, Tafinlar (Dabrafenib), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Thiotepa, Toposar (Etoposide), Topotecan Hydrochloride, Toremifene, Torisel (Temsirolimus), Tositumomab and I 131 Iodine Tositumomab, Totect (Dexrazoxane Hydrochloride), TPF, Trametinib, Trastuzumab, Treanda (Bendamustine Hydrochloride), Trisenox (Arsenic Trioxide), Tykerb (Lapatinib Ditosylate), Vandetanib, VAMP, Vectibix (Panitumumab), VeIP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), XELIRI, Xgeva (Denosumab), Xofigo (Radium 223 Dichloride), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zoladex (Goserelin Acetate), Zoledronic Acid, Zolinza (Vorinostat), Zometa (Zoledronic Acid), Zydelig (Idelalisib), Zykadia (Ceritinib), and Zytiga (Abiraterone Acetate).

In some embodiments, the subject is not administered another therapeutic agent and is administered a composition consisting of or consisting essentially of a fusion protein or viral vector of the invention.

Also provided are methods for predicting and/or evaluating a response to treatment with GRIM-19 by assessing the level of expression of one or more markers associated with exposure to GRIM-19. Such markers may include, but are not limited to, CCL-5, CCL-22, CXCL-1,-2, -3, -4, -5, -7, -9, -10, -11, -12, -13, -14, -15, -16, -17, CX3CL1, CXCR-2, -3, -5, -6, -7, IL-5, IL-17B, IL-12B, TNFS14 (Light), EGFR, Fyn, Matrix Metalloproteases (MMPs) 2, 7, 9, 19, 20, 23, 24, CCL-2, -14, -15, CCR-4, -7, -9 and CXCR4; IL-1 and IL-36.

In some embodiments, the level of expression of one or more of the GRIM-19 markers in a subject may be assessed, and based on the level detected, a decision may be made to treat (or to continue or discontinue treatment) with GRIM-19 or a biologically active fragment or derivative thereof or the fusion proteins or viral vectors of the invention, or to employ an alternate treatment.

In some embodiments, detection or measurement of expression levels is performed as compared to controls, which may include, but are not limited to, a comparison with data from normal subjects and/or comparable normal tissue (in the same or different subjects) absent the disease or disorder present in the subject (or the specific tissue of the subject tested). In some embodiments, the comparison may be between levels detected at a variety of time intervals (and/or locations) in a patient. In some embodiments, the detection needs to be statistically significant as compared to background or control levels; the ability to assess significance is well-known in the art.

In some embodiments, markers that are upregulated in cells which are responsive to GRIM-19 treatment may include one or more of CCL-5, CCL-22, CXCL-1,-2, -3, -4, -5, -7, -9, -10, -11, -12, -13, -14, -15, -16, -17, CX3CL1, CXCR-2, -3, -5, -6, -7, IL-5, IL-17B, IL-12B, TNFS14 (Light), EGFR, Fyn, Matrix Metalloproteases (MMPs) 2, 7, 9, 19, 20, 23, and 24. In some embodiments, markers that are downregulated in cells which are responsive to GRIM-19 may include one or more of CCL-2, -14, -15, CCR-4, -7, -9 and CXCR4; IL-1 and IL-36.

In another embodiment, the invention provides a method of predicting responsiveness of a subject having a disease or condition susceptible to GRIM-19 treatment, comprising
  obtaining the results of an assay from a tissue from the subject that measures the expression level of one or more of CCL-5, CCL-22, CXCL-1,-2, -3, -4, -5, -7, -9, -10, -11, -12, -13, -14, -15, -16, -17, CX3CL1, CXCR-2, -3, -5, -6, -7, IL-5, IL-17B, IL-12B, TNFS14 (Light), EGFR, Fyn, Matrix Metalloproteases (MMPs) 2, 7, 9, 19, 20, 23, and 24, CCL-2, -14, -15, CCR-4, -7, -9 and CXCR4; IL-1 and IL-36;
  wherein responsiveness of the subject to the treatment is predicted when one or more of CCL-5, CCL-22, CXCL-1,-2, -3, -4, -5, -7, -9, -10, -11, -12, -13, -14, -15, -16, -17, CX3CL1, CXCR-2, -3, -5, -6, -7, IL-5, IL-17B, IL-12B, TNFS14 (Light), EGFR, Fyn, Matrix Metalloproteases (MMPs) 2, 7, 9, 19, 20, 23, or 24 is upregulated in the tissue and/or one or more of CCL-2, -14, -15, CCR-4, -7, -9, CXCR4, IL-1 or IL-36 is downregulated in the tissue.

In some embodiments, the method further comprises administering to the subject an effective amount of GRIM-19 or a biologically active fragment or derivative thereof when responsiveness to GRIM-19 treatment is predicted in the subject. In some embodiments, the method further comprises administering to the subject an effective amount of a fusion protein and/or viral vector of the invention when responsiveness to GRIM-19 treatment is predicted in the subject.

In another embodiment, methods of screening for biologically active fragments (including, but not limited to truncations) or derivatives of GRIM-19 are contemplated. In some embodiments, biological activity may be assessed using one of the methods described herein, including detecting changes in the expression of certain marker genes that are responsive to GRIM-19 treatment. Some of the biological activities that can be assessed include, but are not limited to, reducing cell proliferation, increasing cell death, and reducing inflammation.

The present invention is further illustrated by the following Examples. These Examples are provided to aid in the understanding of the invention and are not to be construed as a limitation thereof.

EXAMPLES

Example 1—Administration of Viral Vectors Comprising GRIM-19 Suppresses Tumor Growth and Metastasis Mice were transplanted with HeLa on the dorsal side. 7 weeks later (when palpable tumors developed (to an average size of 0.2 cm$^3$) mice were treated with lentiviruses ($10^8$ particles on 6 different days) expressing either empty vector (EV) or GRIM-19 and tumor growth was measured. It is shown herein that GRIM-19 suppresses tumor growth of human cervical carcinoma cells (HeLa) (FIG. 1A).

Example 2—Loss of GRIM-19 Correlates with Poor Prognosis

Figure 2:
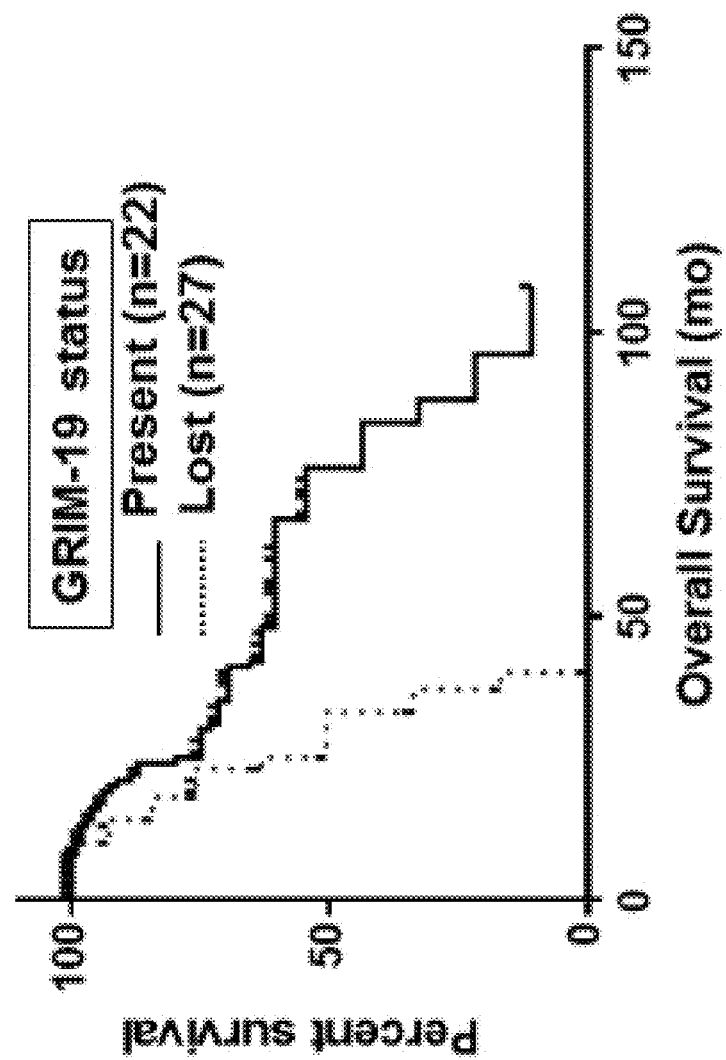
FIG. 2. Kaplan-Meier analyses. Tumor cores from a cohort of patients with HNSCC were screened for GRIM-19 expression using IHC. Blinded samples were scored by two experts. Note the poorer survival of patients, who lost GRIM-19 than those who have GRIM-19.
Figure 3:
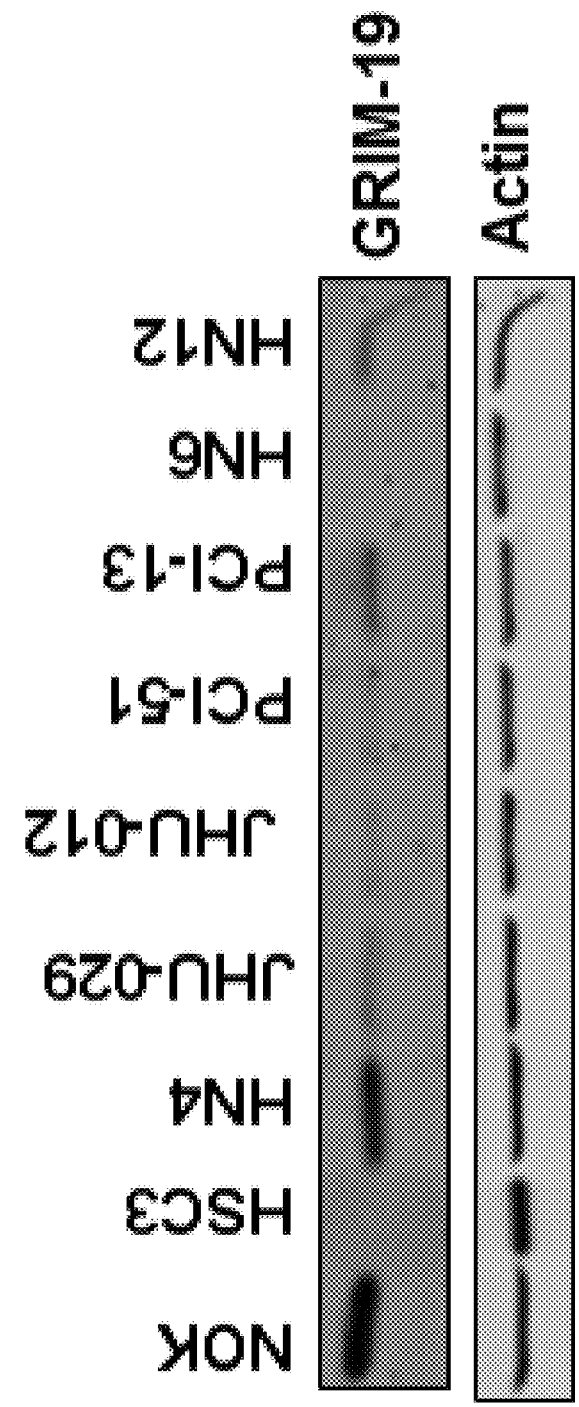
FIG. 3. Loss of GRIM-19 expression in HNSCC lines. Western blot showing GRIM-19 expression. Note the significant loss of GRIM-19 in all most all cell lines compared to the control NOK (Normal Oral Keratinocyte).

GRIM-19 loss in primary HNSCC (FIG. 2) correlated with a poor prognosis (median survival of 33 months vs 76 months in those with GRIM19, hazard ratio of 2.303, p<0.001, Mantel-Cox log rank test). Within this sample, loss of GRIM-19 amounts to 55% of tumors, which does not include other genetic alterations such as mutations or microdeletions. Similarly in another set of 60 tumor tissue microarrays, we have observed loss of GRIM-19 expression in 77% of tumors (not shown). Furthermore, 87% of HNSCC lines (n=16 and all HPV$^{-ve}$), derived from various anatomical positions of head and neck (Larynx, palate, tongue, pharynx etc) exhibited a significant loss of GRIM-19 expression (FIG. 3), compared to a non-oncogenic normal oral keratinocyte (NOK) cells. In two HNSCC cell lines we have observed point mutations in GRIM-19. Thus, GRIM-19 alterations are common in human tumors. These observations highlight the importance of GRIM-19 as an emerging tumor suppressor.

Example 3—Preparation of Recombinant PTD-Tagged GRIM-19

Figure 4:
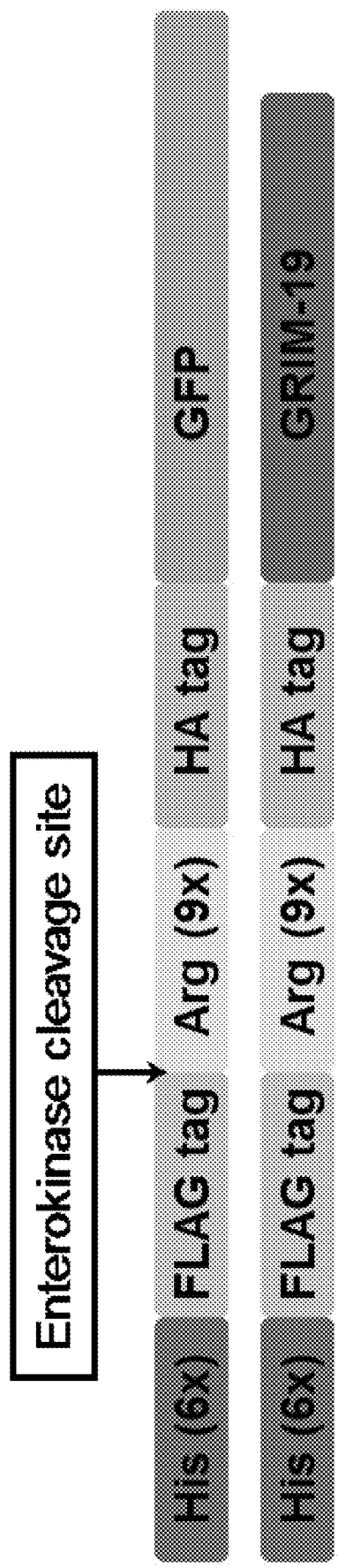
FIG. 4. rGRIM-19 and control constructs. These recombinant proteins were expressed using pET32B+ vector. The His-tag allows the purification of the proteins. Following this protein was purified and treated with enterokinase (a protease) to release His-FLAG tags. The final product will have 9 arginine tag (PTD) and HA-tag which allow the uptake and detection of the protein, respectively.

This example describes the development of a recombinant PTD-tagged-GRIM-19 (rGRIM-19) that could be expressed using both bacterial and baculoviral vectors in large quantities and to high purity (FIG. 4). The fusion protein rGRIM-19 suppresses in vitro tumor cell growth (see FIG. 1B) as well as tumor growth of human prostate cancer cells in mice (see FIG. 1C).

Example 4—GRIM-19$^{-ve}$ Signature can Predict Tumor Cell Responses to Targeted Therapies This example describes an RNA sequence analyses of a human HNSCC line lacking GRIM-19 (HN6) that has been compared to a cell line that has endogenous GRIM-19 (HN4), which has resulted in the identification of a "GRIM-19$^{-ve}$ signature." This designation reflects its origin in GRIM-19 deficient tumors cells (no other contaminating cells). Most proteins identified in this signature are immunomodulatory cytokines and proteins that permit tumor inflammation and metastatic spread of cells (e.g., MMPs)

(FIG. 5). It has been confirmed that this signature is exclusively expressed in tumor cells lacking GRIM-19 but not in normal cells using qPCR (FIG. 6A). More importantly, restoration of GRIM-19 repressed the expression of these genes (FIG. 6B). Indeed, a GRIM-19 dependent expression of these genes was also observed in tumors developed in mice (FIG. 6C). Thus, the GRIM-19$^{-ve}$ signature is useful in predicting tumor cell response to targeted therapies.

Example 5—In Vitro Effects of rGRIM-19

Figure 6:
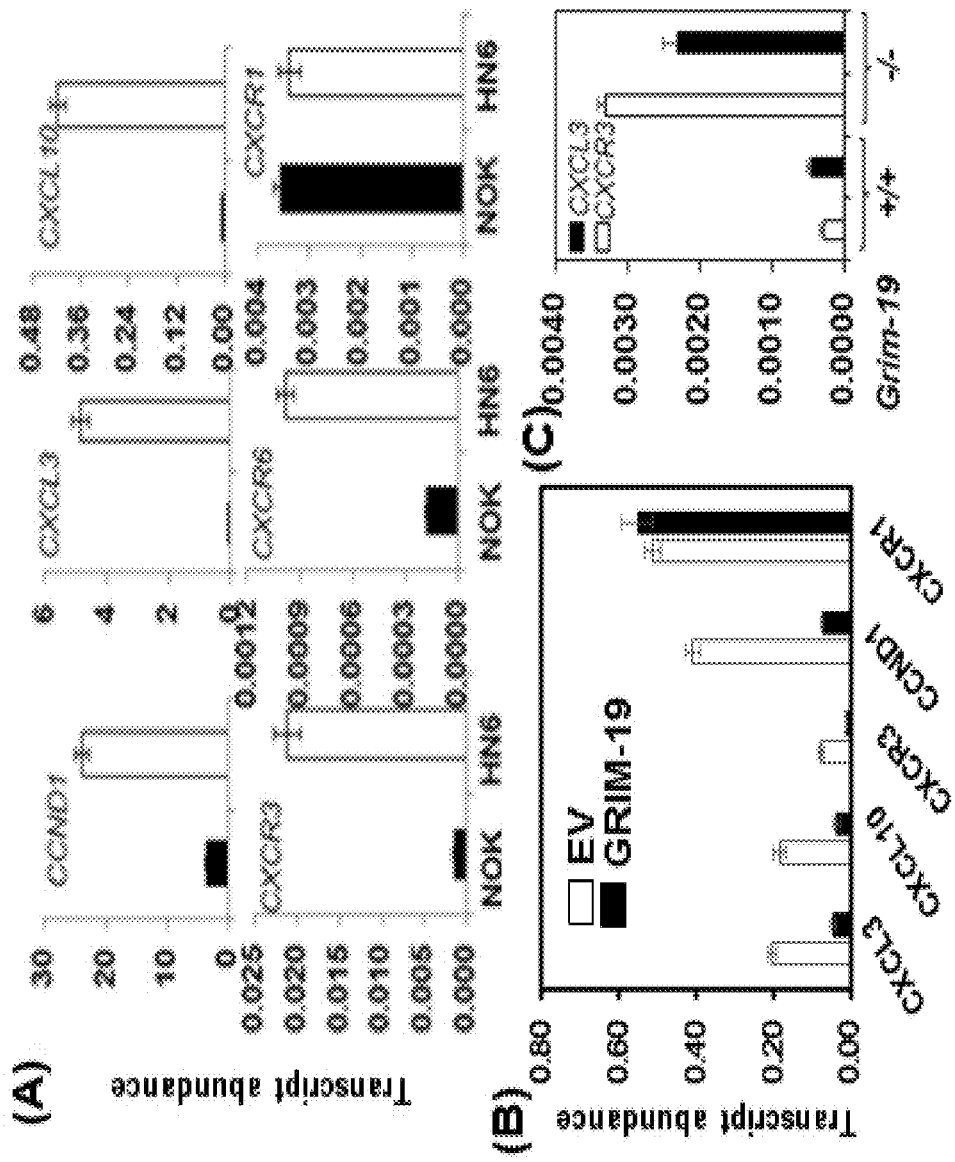
FIG. 6. Loss of GRIM-19 upregulates the expression of chemokines and receptors. HN6: Human tongue SCC (A) q-RT-PCR of specific transcripts. Note the elevated expression of cyclin D1 and specific chemokine genes in HN6. (B) GRIM-19 restoration (lentiviral) into HN6 cells down regulates gene expression. EV: empty vector transduced cells. Note no change in CXCR1 expression in both panels. Mean±SD presented. n=6 in each bar (C) qPCR analyses of the indicated genes in SCC developed in mice with or without Grim-19 gene. Each bar shows mean±SD of 3 tumors from separate mice. Five replicates were run for each tumor sample.

To test its global growth suppressive effects, several HNSCC lines (with low GRIM-19 levels, n=8) are treated with various doses of rGRIM-19 (1 µg-50 µg/ml) and its impact on controlling the GRIM-19$^{-ve}$ signature using qPCR is measured. The selected tumor cell lines will represent the heterogeneity of the HNSCCs for they were isolated from tumors originating in various regions of oral cavity (larynx, tongue, pharynx, palate, etc). As a control, a similarly tagged green fluorescent protein (GFP) is used. Cells are transfected with a lentivirus expressing GRIM-19 as a positive control in these experiments (FIG. 6). A negative control NOK cells (FIG. 3) is also used to demonstrate a lack of an effect of rGRIM-19 (FIG. 1). Expression of the proteins corresponding to the Grim-19$^{-ve}$ signature (only those proteins induced in majority samples and showed a GRIM-19-dependence) are also determined using ELISA kits (R&D Systems, Inc.) in cell supernatants, and in cell extracts using Western blotting. Since GRIM-19 also induces growth suppression, the effect of rGRIM-19 on cell growth and apoptosis is determined as described in previous studies (Zhang et al., (2008), *Clin Cancer Res* 14, 559-568; Kalakonda et al., (2007), *Am J Pathol* 171, 1352-1368; Zhang et al., (2007), *Cancer Res* 67, 5859-5864).

To further confirm these results patient derived xenograft (PDX) lines are screened (e.g., 4 HNSCC PDX) lines. A portion of these cells are treated in vitro with rGRIM-19 for up to 5 days with various doses (1-50 µg/ml).

Example 6—In Vivo Effects of rGRIM-19

Figure 7:
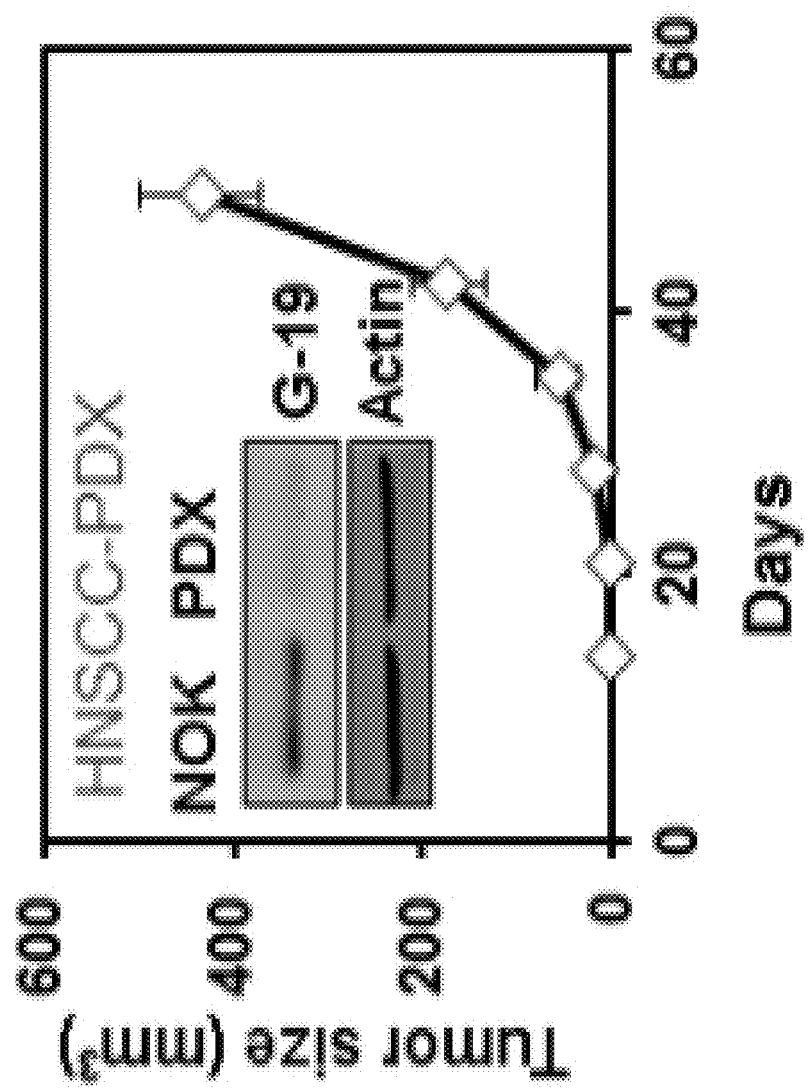
FIG. 7. HNSCC-PDX: Cells ($10^6$) from a human primary oral squamous cell carcinoma (OSCC) tumor were transplanted subcutaneously into NSG mice (n=6) and tumor growth was monitored. Insets show the expression of GRIM-19 in the PDX as compared to Normal Oral Keratinocytes (NOK).

In the next set of experiments in vivo effects of rGRIM-19 are examined. Two tumor models are used: 1) a mouse oral cancer model and 2) human HNSCC PDX tumor model (FIG. 7). A monoallelic loss of GRIM-19 is sufficient promote tumorigenesis, in the mouse oral cancer model, heterozygotes are also used. Since these are conditional KO mice ($^{f/f}$), to delete Grim-19, groups (n=45/genotype) of Grim-19$^{+/f}$/K14-Cre-ER$^{tam}$ (GRIM-19$^{+/-}$) and Grim-19$^{f/f}$/K14-Cre-ER$^{tam}$ (Grim-19$^{-/-}$) mice are painted in the oral cavity with 4-hydoxy tamoxifen (activates the cre-recombinase) in peanut oil daily for 1 week (Raimondi et al., (2009), *Cancer Res* 69, 4159-4166). Because K14 does not significantly express in other tissues, it is expected that Grim-19 will be deleted in oral epithelium. Mice will be fed with NQO (20 µg/ml in drinking water) for 16 weeks and monitored for frequency, sizes, and kinetics of tumor development (Czerninski et al., (2009), *Cancer Prev Res (Phila)* 2, 27-36; Vitale-Cross et al., (2009), *Cancer Prev Res (Phila)* 2, 419-422; Wong, K. K., (2009), *Cancer Prev Res (Phila)* 2, 10-13). Both male and female mice are used to a avoid gender bias in the data collected. For each genotype a group of mice (n=10) without NQO-treatment is used as controls. Each NQO-treated mouse develops on average 4 tumors, which is sufficient for discriminating the groups. Tumor bearing mice are treated as following after stratifying into three groups: 1) no treatment, 2) GFP, 3) rGRIM-19. All treatments are given in the juxta tumoral areas (500 µg/60 µl/mouse) thrice a week for 2 months. This dosing is based on an ongoing prostate cancer xenograft experiment (not shown). Tumor numbers and sizes are measured at the end of the experiment. Tumors are resected and expression of GRIM-19$^{-ve}$ signature is examined using qPCR and Western blots. Peripheral blood from these animals is assayed for cytokine and chemokine levels using commercially available ELISA kits (R&D systems).

Example 7—Effects of rGRIM-19 in the PDX Models

Tumor cells (1×10$^6$) are injected subcutaneously into NSG (NOD.Cg Prkde$^{scid}$ Il2rg$^{tmIWjl}$/SzJ) mice (n=30). Following the development of palpable tumors (FIG. 7), mice are treated (n=10/treatment group) with: 1) none, 2) rGFP, 3) rGRIM-19 as above. Four different PDXs are used for these studies. Tumor size, apoptosis (TUNEL) are measured as previously (Zhang et al., (2008), *Clin Cancer Res* 14, 559-568; Nallar et al., (2010), *Am J Pathol* 177, 896-907; Zhang et al., (2007), *Cancer Res* 67, 5859-5864). Tumor RNAs are quantified for the expression of the GRIM-19$^{-ve}$ signature.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

What is claimed is:

1. A method of treating a GRIM-19 negative cancer in a subject, comprising:

obtaining the results of an assay that measures the expression level in cancer tissue of one or more of CCL-5, CCL-22, CXCL-1, CXCL-2, CXCL-3, CXCL-4, CXCL-5, CXCL-7, CXCL-9, CXCL-10, CXCL-11, CXCL-12, CXCL-13, CXCL-14, CXCL-15, CXCL-16, CXCL-17, CX3CL1, CXCR-2, CXCR-3, CXCR-5, CXCR-6, CXCR-7, IL5, IL17B, IL-12B, TNFS14 (Light), EGFR, Fyn, MMP-7, MMP-19, MMP-20, MMP-23, MMP-24, CCL-2, CCL-14, CCL-15, CCR-4, CCR-7, CCR-9, CXCR-4, IL-1 and IL-36;

wherein positive responsiveness of the subject to the treatment is predicted when one or more of the CCL-5, the CCL-22, the CXCL-1, the CXCL-2, the CXCL-3, the CXCL-4, the CXCL-5, the CXCL-7, the CXCL-9, the CXCL-10, the CXCL-11, the CXCL-12, the CXCL-13, the CXCL-14, the CXCL-15, the CXCL-16, the CXCL-17, the CX3CL1, the CXCR-2, the CXCR-3, the CXCR-5, the CXCR-6, the CXCR-7, the IL5, the IL17B, the IL-12B, the TNFS14 (Light), the EGFR, the Fyn, the MMP-7, the MMP-19, the MMP-20, the MMP-23 and the MMP-24 is upregulated in the cancer tissue and/or one or more of the CCL-2, the CCL-14, the CCL-15, the CCR-4, the CCR-7, the CCR-9, the CXCR4, the IL-1 and the IL-36 is downregulated in the cancer tissue as measured in the assay, relative to non-cancerous correlative tissue, wherein the treatment comprises directly administering to the cancer tissue a pharmaceutical composition comprising a fusion protein comprising GRIM-19 protein with an amino acid sequence of SEQ ID NO:11 or a derivative thereof having at least 99% identity to SEQ ID NO:11, linked to a protein transduction domain.

2. The method of claim 1, wherein the cancer is selected from the group consisting of head and neck cancer, oral cancer and prostate cancer.

3. The method of claim 1, wherein the subject is administered the composition in combination with at least one of one or more additional cancer therapeutics and radiotherapy.

* * * * *

SEQUENCE LISTING

```
<160> NUMBER OF SEQ ID NOS: 59

<210> SEQ ID NO 1
<211> LENGTH: 435
<212> TYPE: DNA
<213> ORGANISM: Homo sapiens

<400> SEQUENCE: 1
atggcggcgt caaaggtgaa gcaggacatg cctccgccgg ggggctatgg gcccatcgac      60
tacaaacgga acttgccgcg tcgaggactg tcgggctaca gcatgctggc catagggatt     120
```

-continued

```
ggaaccctga tctacgggca ctggagcata atgaagtgga accgtgagcg caggcgccta    180
caaatcgagg acttcgaggc tcgcatcgcg ctgttgccac tgttacaggc agaaaccgac    240
cggaggacct tgcagatgct tcgggagaac ctggaggagg aggccatcat catgaaggac    300
gtgcccgact ggaaggtggg ggagtctgtg ttccacacaa cccgctgggt gccccccttg    360
atcggggagc tgtacgggct gcgcaccaca gaggaggctc tccatgccag ccacggcttc    420
atgtggtaca cgtag                                                    435
```

<210> SEQ ID NO 2
<211> LENGTH: 66
<212> TYPE: DNA
<213> ORGANISM: Artificial sequence
<220> FEATURE:
<223> OTHER INFORMATION: PTD sequence

<400> SEQUENCE: 2

```
agacgaaggc gcagacggag gcgtagaccg tctgccagct atccatacga cgtgcctgac    60
tacgcg                                                              66
```

<210> SEQ ID NO 3
<211> LENGTH: 22
<212> TYPE: PRT
<213> ORGANISM: Artificial sequence
<220> FEATURE:
<223> OTHER INFORMATION: PTD sequence

<400> SEQUENCE: 3

Arg Arg Arg Arg Arg Arg Arg Arg Arg Pro Ser Ala Ser Tyr Pro Tyr
1               5                   10                  15

Asp Val Pro Asp Tyr Ala
            20

<210> SEQ ID NO 4
<211> LENGTH: 30
<212> TYPE: DNA
<213> ORGANISM: Artificial sequence
<220> FEATURE:
<223> OTHER INFORMATION: PTD sequence

<400> SEQUENCE: 4

```
ggccgtaaaa aacgccgtca acgccgccgt                                    30
```

<210> SEQ ID NO 5
<211> LENGTH: 10
<212> TYPE: PRT
<213> ORGANISM: Artificial sequence
<220> FEATURE:
<223> OTHER INFORMATION: PTD sequence

<400> SEQUENCE: 5

Gly Arg Lys Lys Arg Arg Gln Arg Arg Arg
1               5                   10

<210> SEQ ID NO 6
<211> LENGTH: 33
<212> TYPE: DNA
<213> ORGANISM: Artificial sequence
<220> FEATURE:
<223> OTHER INFORMATION: PTD sequence

<400> SEQUENCE: 6

```
tatggccgta aaaaacgccg tcaacgccgc cgt                                33
```

<210> SEQ ID NO 7
<211> LENGTH: 11
<212> TYPE: PRT
<213> ORGANISM: Artificial sequence
<220> FEATURE:
<223> OTHER INFORMATION: PTD sequence

<400> SEQUENCE: 7

Tyr Gly Arg Lys Lys Arg Arg Gln Arg Arg Arg
1               5                   10

<210> SEQ ID NO 8
<211> LENGTH: 21
<212> TYPE: DNA
<213> ORGANISM: Artificial sequence
<220> FEATURE:
<223> OTHER INFORMATION: PTD sequence

<400> SEQUENCE: 8
ggccgtaaaa aacgccgtca a                                              21

<210> SEQ ID NO 9
<211> LENGTH: 7
<212> TYPE: PRT
<213> ORGANISM: Artificial sequence
<220> FEATURE:
<223> OTHER INFORMATION: PTD sequence

<400> SEQUENCE: 9

Gly Arg Lys Lys Arg Arg Gln
1               5

<210> SEQ ID NO 10
<211> LENGTH: 579
<212> TYPE: DNA
<213> ORGANISM: Artificial sequence
<220> FEATURE:
<223> OTHER INFORMATION: Cell-Penetrating Peptide (CPP)-tagged human
      GRIM-19

<400> SEQUENCE: 10
atggcacatc accaccacca tcacgtgggt accggttcga atgatgacga cgacaagagt        60
ccggatagac gaaggcgcag acggaggcgt agaccgtctg ccagctatcc atacgacgtg       120
cctgactacg cgaggctgca attcatggcg gcgtcaaagg tgaagcagga catgcctccg       180 ccgggggggct atgggcccat cgactacaaa cggaacttgc cgcgtcgagg actgtcgggc     240
tacagcatgc tggccatagg gattggaacc ctgatctacg ggcactggag cataatgaag       300
tggaaccgtg agcgcaggcg cctacaaatc gaggacttcg aggctcgcat cgcgctgttg       360
ccactgttac aggcagaaac cgaccggagg accttgcaga tgcttcggga gaacctggag       420
gaggaggcca tcatcatgaa ggacgtgccc gactggaagg tgggggagtc tgtgttccac       480
acaacccgct gggtgccccc cttgatcggg gagctgtacg gctgcgcac cacagaggag       540 gctctccatg ccagccacgg cttcatgtgg tacacgtag                              579

<210> SEQ ID NO 11
<211> LENGTH: 144
<212> TYPE: PRT
<213> ORGANISM: Homo sapiens

<400> SEQUENCE: 11

Met Ala Ala Ser Lys Val Lys Gln Asp Met Pro Pro Gly Gly Tyr
1               5                   10                  15

Gly Pro Ile Asp Tyr Lys Arg Asn Leu Pro Arg Arg Gly Leu Ser Gly
            20                  25                  30

Tyr Ser Met Leu Ala Ile Gly Ile Gly Thr Leu Ile Tyr Gly His Trp
        35                  40                  45

Ser Ile Met Lys Trp Asn Arg Glu Arg Arg Leu Gln Ile Glu Asp
    50                  55                  60

Phe Glu Ala Arg Ile Ala Leu Leu Pro Leu Leu Gln Ala Glu Thr Asp
65              70                  75                  80

Arg Arg Thr Leu Gln Met Leu Arg Glu Asn Leu Glu Glu Glu Ala Ile
                85                  90                  95

Ile Met Lys Asp Val Pro Asp Trp Lys Val Gly Glu Ser Val Phe His
            100                 105                 110

Thr Thr Arg Trp Val Pro Leu Ile Gly Glu Leu Tyr Gly Leu Arg
        115                 120                 125

Thr Thr Glu Glu Ala Leu His Ala Ser His Gly Phe Met Trp Tyr Thr
130                 135                 140

<210> SEQ ID NO 12
<211> LENGTH: 192
<212> TYPE: PRT
<213> ORGANISM: Artificial sequence
<220> FEATURE:
<223> OTHER INFORMATION: Cell-Penetrating Peptide (CPP)-tagged human
      GRIM-19

<400> SEQUENCE: 12

Met Ala His His His His His Val Gly Thr Gly Ser Asn Asp Asp
1               5                   10                  15

Asp Asp Lys Ser Pro Asp Arg Arg Arg Arg Arg Arg Arg Pro
            20                  25                  30

Ser Ala Ser Tyr Pro Tyr Asp Val Pro Asp Tyr Ala Arg Leu Gln Phe
        35                  40                  45

Met Ala Ala Ser Lys Val Lys Gln Asp Met Pro Pro Gly Gly Tyr
    50                  55                  60

Gly Pro Ile Asp Tyr Lys Arg Asn Leu Pro Arg Arg Gly Leu Ser Gly
65              70                  75                  80

Tyr Ser Met Leu Ala Ile Gly Ile Gly Thr Leu Ile Tyr Gly His Trp
                85                  90                  95

Ser Ile Met Lys Trp Asn Arg Glu Arg Arg Arg Leu Gln Ile Glu Asp
            100                 105                 110

Phe Glu Ala Arg Ile Ala Leu Leu Pro Leu Leu Gln Ala Glu Thr Asp
        115                 120                 125

Arg Arg Thr Leu Gln Met Leu Arg Glu Asn Leu Glu Glu Glu Ala Ile
130                 135                 140

Ile Met Lys Asp Val Pro Asp Trp Lys Val Gly Glu Ser Val Phe His
145                 150                 155                 160

Thr Thr Arg Trp Val Pro Leu Ile Gly Glu Leu Tyr Gly Leu Arg
            165                 170                 175

Thr Thr Glu Glu Ala Leu His Ala Ser His Gly Phe Met Trp Tyr Thr
        180                 185                 190

<210> SEQ ID NO 13

```
<211> LENGTH: 16
<212> TYPE: PRT
<213> ORGANISM: Artificial sequence
<220> FEATURE:
<223> OTHER INFORMATION: PTD sequence

<400> SEQUENCE: 13

Arg Gln Ile Lys Ile Trp Phe Gln Asn Arg Arg Met Lys Trp Lys Lys
1               5                   10                  15

<210> SEQ ID NO 14
<211> LENGTH: 7
<212> TYPE: PRT
<213> ORGANISM: Artificial sequence
<220> FEATURE:
<223> OTHER INFORMATION: PTD sequence

<400> SEQUENCE: 14

Arg Arg Met Lys Trp Lys Lys
1               5

<210> SEQ ID NO 15
<211> LENGTH: 16
<212> TYPE: PRT
<213> ORGANISM: Artificial sequence
<220> FEATURE:
<223> OTHER INFORMATION: PTD sequence

<400> SEQUENCE: 15

Arg Arg Trp Arg Arg Trp Trp Arg Arg Trp Trp Arg Arg Trp Arg Arg
1               5                   10                  15

<210> SEQ ID NO 16
<211> LENGTH: 18
<212> TYPE: PRT
<213> ORGANISM: Artificial sequence
<220> FEATURE:
<223> OTHER INFORMATION: PTD sequence

<400> SEQUENCE: 16

Arg Gly Gly Arg Leu Ser Tyr Ser Arg Arg Phe Ser Thr Ser Thr
1               5                   10                  15

Gly Arg

<210> SEQ ID NO 17
<211> LENGTH: 9
<212> TYPE: PRT
<213> ORGANISM: Artificial sequence
<220> FEATURE:
<223> OTHER INFORMATION: PTD sequence

<400> SEQUENCE: 17

Arg Lys Lys Arg Arg Gln Arg Arg Arg
1               5

<210> SEQ ID NO 18
<211> LENGTH: 11
<212> TYPE: PRT
<213> ORGANISM: Artificial sequence
<220> FEATURE:
<223> OTHER INFORMATION: PTD sequence

<400> SEQUENCE: 18

Tyr Ala Arg Ala Ala Ala Arg Gln Ala Arg Ala
1               5                   10
```

-continued

```
<210> SEQ ID NO 19
<211> LENGTH: 8
<212> TYPE: PRT
<213> ORGANISM: Artificial sequence
<220> FEATURE:
<223> OTHER INFORMATION: PTD sequence

<400> SEQUENCE: 19

Arg Arg Arg Arg Arg Arg Arg Arg
1               5

<210> SEQ ID NO 20
<211> LENGTH: 8
<212> TYPE: PRT
<213> ORGANISM: Artificial sequence
<220> FEATURE:
<223> OTHER INFORMATION: PTD sequence

<400> SEQUENCE: 20

Lys Lys Lys Lys Lys Lys Lys Lys
1               5

<210> SEQ ID NO 21
<211> LENGTH: 27
<212> TYPE: PRT
<213> ORGANISM: Artificial sequence
<220> FEATURE:
<223> OTHER INFORMATION: PTD sequence
<220> FEATURE:
<221> NAME/KEY: misc_feature
<222> LOCATION: (25)..(25)
<223> OTHER INFORMATION: Xaa can be any naturally occurring amino acid

<400> SEQUENCE: 21

Gly Trp Thr Leu Asn Ser Ala Gly Tyr Leu Leu Gly Lys Ile Asn Leu
1               5                   10                  15

Lys Ala Leu Ala Ala Leu Ala Lys Xaa Ile Leu
            20                  25

<210> SEQ ID NO 22
<211> LENGTH: 16
<212> TYPE: PRT
<213> ORGANISM: Artificial sequence
<220> FEATURE:
<223> OTHER INFORMATION: PTD sequence

<400> SEQUENCE: 22

Ser Arg Arg His His Cys Arg Ser Lys Ala Lys Arg Ser Arg His His
1               5                   10                  15

<210> SEQ ID NO 23
<211> LENGTH: 11
<212> TYPE: PRT
<213> ORGANISM: Artificial sequence
<220> FEATURE:
<223> OTHER INFORMATION: PTD sequence

<400> SEQUENCE: 23

Asn Arg Ala Arg Arg Asn Arg Arg Arg Val Arg
1               5                   10

<210> SEQ ID NO 24
<211> LENGTH: 15
<212> TYPE: PRT
<213> ORGANISM: Artificial sequence
<220> FEATURE:
<223> OTHER INFORMATION: PTD sequence
```

```
<400> SEQUENCE: 24

Arg Gln Leu Arg Ile Ala Gly Arg Arg Leu Arg Gly Arg Ser Arg
1               5                   10                  15

<210> SEQ ID NO 25
<211> LENGTH: 13
<212> TYPE: PRT
<213> ORGANISM: Artificial sequence
<220> FEATURE:
<223> OTHER INFORMATION: PTD sequence

<400> SEQUENCE: 25

Lys Leu Ile Lys Gly Arg Thr Pro Ile Lys Phe Gly Lys
1               5                   10

<210> SEQ ID NO 26
<211> LENGTH: 10
<212> TYPE: PRT
<213> ORGANISM: Artificial sequence
<220> FEATURE:
<223> OTHER INFORMATION: PTD sequence

<400> SEQUENCE: 26

Arg Arg Ile Pro Asn Arg Arg Pro Arg Arg
1               5                   10

<210> SEQ ID NO 27
<211> LENGTH: 18
<212> TYPE: PRT
<213> ORGANISM: Artificial sequence
<220> FEATURE:
<223> OTHER INFORMATION: PTD sequence

<400> SEQUENCE: 27

Lys Leu Ala Leu Lys Leu Ala Leu Lys Ala Leu Lys Ala Ala Leu Lys
1               5                   10                  15

Leu Ala

<210> SEQ ID NO 28
<211> LENGTH: 14
<212> TYPE: PRT
<213> ORGANISM: Artificial sequence
<220> FEATURE:
<223> OTHER INFORMATION: PTD sequence

<400> SEQUENCE: 28

Lys Leu Ala Lys Leu Ala Lys Lys Leu Ala Lys Leu Ala Lys
1               5                   10

<210> SEQ ID NO 29
<211> LENGTH: 27
<212> TYPE: PRT
<213> ORGANISM: Artificial sequence
<220> FEATURE:
<223> OTHER INFORMATION: PTD sequence

<400> SEQUENCE: 29

Gly Ala Leu Phe Leu Gly Phe Leu Gly Ala Ala Gly Ser Thr Asn Gly
1               5                   10                  15

Ala Trp Ser Gln Pro Lys Lys Lys Arg Lys Val
            20                  25

<210> SEQ ID NO 30
<211> LENGTH: 21
<212> TYPE: PRT
```

```
<213> ORGANISM: Artificial sequence
<220> FEATURE:
<223> OTHER INFORMATION: PTD sequence

<400> SEQUENCE: 30

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 31
<211> LENGTH: 20
<212> TYPE: PRT
<213> ORGANISM: Artificial sequence
<220> FEATURE:
<223> OTHER INFORMATION: PTD sequence

<400> SEQUENCE: 31

Leu Lys Lys Leu Leu Lys Lys Leu Leu Lys Lys Leu Leu Lys Lys Leu
1               5                   10                  15

Leu Lys Lys Leu
            20

<210> SEQ ID NO 32
<211> LENGTH: 34
<212> TYPE: PRT
<213> ORGANISM: Artificial sequence
<220> FEATURE:
<223> OTHER INFORMATION: PTD sequence

<400> SEQUENCE: 32

Gln Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 33
<211> LENGTH: 23
<212> TYPE: PRT
<213> ORGANISM: Artificial sequence
<220> FEATURE:
<223> OTHER INFORMATION: PTD sequence

<400> SEQUENCE: 33

Met Gly Leu Gly Leu His Leu Leu Val Leu Ala Ala Ala Leu Gln Gly
1               5                   10                  15

Ala Lys Ser Lys Arg Lys Val
            20

<210> SEQ ID NO 34
<211> LENGTH: 26
<212> TYPE: PRT
<213> ORGANISM: Artificial sequence
<220> FEATURE:
<223> OTHER INFORMATION: PTD sequence

<400> SEQUENCE: 34

Ala Ala Val Ala Leu Leu Pro Ala Val Leu Leu Ala Leu Leu Ala Pro
1               5                   10                  15

Ala Ala Ala Asn Tyr Lys Lys Pro Lys Leu
            20                  25
```

```
<210> SEQ ID NO 35
<211> LENGTH: 28
<212> TYPE: PRT
<213> ORGANISM: Artificial sequence
<220> FEATURE:
<223> OTHER INFORMATION: PTD sequence

<400> SEQUENCE: 35

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 36
<211> LENGTH: 24
<212> TYPE: PRT
<213> ORGANISM: Artificial sequence
<220> FEATURE:
<223> OTHER INFORMATION: PTD domain

<400> SEQUENCE: 36

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 37
<211> LENGTH: 26
<212> TYPE: PRT
<213> ORGANISM: Artificial sequence
<220> FEATURE:
<223> OTHER INFORMATION: PTD sequence
<220> FEATURE:
<221> NAME/KEY: misc_feature
<222> LOCATION: (24)..(24)
<223> OTHER INFORMATION: Xaa can be any naturally occurring amino acid

<400> SEQUENCE: 37

Asp Pro Lys Gly Asp Pro Lys Gly Val Thr Val Thr Val Thr Val Thr
1               5                   10                  15

Val Thr Gly Lys Gly Asp Pro Xaa Pro Asp
            20                  25

<210> SEQ ID NO 38
<211> LENGTH: 14
<212> TYPE: PRT
<213> ORGANISM: Artificial sequence
<220> FEATURE:
<223> OTHER INFORMATION: PTD sequence

<400> SEQUENCE: 38

Pro Pro Pro Pro Pro Pro Pro Pro Pro Pro Pro Pro Pro Pro
1               5                   10

<210> SEQ ID NO 39
<211> LENGTH: 18
<212> TYPE: PRT
<213> ORGANISM: Artificial sequence
<220> FEATURE:
<223> OTHER INFORMATION: PTD sequence

<400> SEQUENCE: 39

Val Arg Leu Pro Pro Pro Val Arg Leu Pro Pro Pro Val Arg Leu Pro
1               5                   10                  15

Pro Pro
```

<210> SEQ ID NO 40
<211> LENGTH: 10
<212> TYPE: PRT
<213> ORGANISM: Artificial sequence
<220> FEATURE:
<223> OTHER INFORMATION: PTD sequence

<400> SEQUENCE: 40

Pro Arg Pro Leu Pro Pro Pro Arg Pro Gly
1               5                   10

<210> SEQ ID NO 41
<211> LENGTH: 30
<212> TYPE: PRT
<213> ORGANISM: Artificial sequence
<220> FEATURE:
<223> OTHER INFORMATION: PTD sequence

<400> SEQUENCE: 41

Ser Val Arg Arg Arg Pro Arg Pro Pro Tyr Leu Pro Arg Pro Arg Pro
1               5                   10                  15

Pro Pro Phe Phe Pro Pro Arg Leu Pro Pro Arg Ile Pro Pro
            20                  25                  30

<210> SEQ ID NO 42
<211> LENGTH: 21
<212> TYPE: PRT
<213> ORGANISM: Artificial sequence
<220> FEATURE:
<223> OTHER INFORMATION: PTD sequence

<400> SEQUENCE: 42

Thr Arg Ser Ser Arg Ala Gly Leu Gln Phe Pro Val Gly Arg Val His
1               5                   10                  15

Arg Leu Leu Arg Lys
            20

<210> SEQ ID NO 43
<211> LENGTH: 23
<212> TYPE: PRT
<213> ORGANISM: Artificial sequence
<220> FEATURE:
<223> OTHER INFORMATION: PTD sequence

<400> SEQUENCE: 43

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 44
<211> LENGTH: 37
<212> TYPE: PRT
<213> ORGANISM: Artificial sequence
<220> FEATURE:
<223> OTHER INFORMATION: PTD sequence

<400> SEQUENCE: 44

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Gly Gln Ala
            20                  25                  30

Thr Gln Ile Ala Lys
            35

<210> SEQ ID NO 45
<211> LENGTH: 28
<212> TYPE: PRT
<213> ORGANISM: Artificial sequence
<220> FEATURE:
<223> OTHER INFORMATION: PTD sequence

<400> SEQUENCE: 45

Ala Leu Trp Met Thr Leu Leu Lys Lys Val Leu Lys Ala Ala Ala Lys
1               5                   10                  15
Ala Ala Leu Asn Ala Val Leu Val Gly Ala Asn Ala
            20                  25

<210> SEQ ID NO 46
<211> LENGTH: 26
<212> TYPE: PRT
<213> ORGANISM: Artificial sequence
<220> FEATURE:
<223> OTHER INFORMATION: PTD sequence

<400> SEQUENCE: 46

Gly Ile Gly Ala Val Leu Lys Val Leu Thr Thr Gly Leu Pro Ala Leu
1               5                   10                  15
Ile Ser Trp Ile Lys Arg Lys Arg Gln Gln
            20                  25

<210> SEQ ID NO 47
<211> LENGTH: 14
<212> TYPE: PRT
<213> ORGANISM: Artificial sequence
<220> FEATURE:
<223> OTHER INFORMATION: PTD sequence

<400> SEQUENCE: 47

Ile Asn Leu Lys Ala Leu Ala Ala Leu Ala Lys Lys Ile Leu
1               5                   10

<210> SEQ ID NO 48
<211> LENGTH: 33
<212> TYPE: PRT
<213> ORGANISM: Artificial sequence
<220> FEATURE:
<223> OTHER INFORMATION: PTD sequence

<400> SEQUENCE: 48

Gly Phe Phe Ala Leu Ile Pro Lys Ile Ile Ser Ser Pro Leu Pro Lys
1               5                   10                  15
Thr Leu Leu Ser Ala Val Gly Ser Ala Leu Gly Gly Ser Gly Gly Gln
            20                  25                  30
Glu

<210> SEQ ID NO 49
<211> LENGTH: 15
<212> TYPE: PRT
<213> ORGANISM: Artificial sequence
<220> FEATURE:
<223> OTHER INFORMATION: PTD sequence

<400> SEQUENCE: 49

Leu Ala Lys Trp Ala Leu Lys Gln Gly Phe Ala Lys Leu Lys Ser
1               5                   10                  15

<210> SEQ ID NO 50

```
<211> LENGTH: 27
<212> TYPE: PRT
<213> ORGANISM: Artificial sequence
<220> FEATURE:
<223> OTHER INFORMATION: PTD sequence
<220> FEATURE:
<221> NAME/KEY: misc_feature
<222> LOCATION: (23)..(23)
<223> OTHER INFORMATION: Xaa can be any naturally occurring amino acid

<400> SEQUENCE: 50

Ser Met Ala Gln Asp Ile Ile Ser Thr Ile Gly Asp Leu Val Lys Trp
1               5                   10                  15

Ile Ile Gln Thr Val Asn Xaa Phe Thr Lys Lys
            20                  25

<210> SEQ ID NO 51
<211> LENGTH: 41
<212> TYPE: PRT
<213> ORGANISM: Artificial sequence
<220> FEATURE:
<223> OTHER INFORMATION: PTD sequence

<400> SEQUENCE: 51

Leu Leu Gly Asp Phe Phe Arg Lys Ser Lys Glu Lys Ile Gly Lys Glu
1               5                   10                  15

Phe Lys Arg Ile Val Gln Arg Ile Lys Gln Arg Ile Lys Asp Phe Leu
            20                  25                  30

Ala Asn Leu Val Pro Arg Thr Glu Ser
        35                  40

<210> SEQ ID NO 52
<211> LENGTH: 18
<212> TYPE: PRT
<213> ORGANISM: Artificial sequence
<220> FEATURE:
<223> OTHER INFORMATION: PTD sequence

<400> SEQUENCE: 52

Pro Ala Trp Arg Lys Ala Phe Arg Trp Ala Trp Arg Met Leu Lys Lys
1               5                   10                  15

Ala Ala

<210> SEQ ID NO 53
<211> LENGTH: 18
<212> TYPE: PRT
<213> ORGANISM: Artificial sequence
<220> FEATURE:
<223> OTHER INFORMATION: PTD sequence

<400> SEQUENCE: 53

Lys Leu Lys Leu Lys Leu Lys Leu Lys Leu Lys Leu Lys Leu Lys Leu
1               5                   10                  15

Lys Leu

<210> SEQ ID NO 54
<211> LENGTH: 18
<212> TYPE: PRT
<213> ORGANISM: Artificial sequence
<220> FEATURE:
<223> OTHER INFORMATION: PTD sequence
```

<400> SEQUENCE: 54

Leu Leu Ile Leu Leu Arg Arg Arg Ile Arg Lys Gln Ala Asn Ala His
1               5                   10                  15

Ser Lys

<210> SEQ ID NO 55
<211> LENGTH: 23
<212> TYPE: PRT
<213> ORGANISM: Artificial sequence
<220> FEATURE:
<223> OTHER INFORMATION: PTD sequence

<400> SEQUENCE: 55

Gly Ala Leu Phe Leu Gly Trp Leu Gly Ala Ala Gly Ser Thr Met Gly
1               5                   10                  15

Ala Lys Lys Lys Arg Lys Val
            20

<210> SEQ ID NO 56
<211> LENGTH: 489
<212> TYPE: DNA
<213> ORGANISM: Artificial sequence
<220> FEATURE:
<223> OTHER INFORMATION: Myc epitope-tagged human GRIM-19

<400> SEQUENCE: 56
atggcggcgt caaaggtgaa gcaggacatg cctccgccgg ggggctatgg gcccatcgac      60
tacaaacgga acttgccgcg tcgaggactg tcgggctaca gcatgctggc catagggatt     120
ggaaccctga tctacgggca ctggagcata atgaagtgga accgtgagcg caggcgccta     180
caaatcgagg acttcgaggc tcgcatcgcg ctgttgccac tgttacaggc agaaaccgac     240
cggaggacct tgcagatgct tcgggagaac ctggaggagg aggccatcat catgaaggac     300
gtgcccgact ggaaggtggg ggagtctgtg ttccacacaa cccgctgggt gccccccttg     360
atcggggagc tgtacgggct gcgcaccaca gaggaggctc tccatgccag ccacggcttc     420
atgtggtaca cgggatccgc ggccgcggaa caaaaactca tctcagaaga ggatctggcg     480
gccgcatag                                                             489

<210> SEQ ID NO 57
<211> LENGTH: 162
<212> TYPE: PRT
<213> ORGANISM: Artificial sequence
<220> FEATURE:
<223> OTHER INFORMATION: Myc epitope-tagged human GRIM-19

<400> SEQUENCE: 57

Met Ala Ala Ser Lys Val Lys Gln Asp Met Pro Pro Gly Gly Tyr
1               5                   10                  15

Gly Pro Ile Asp Tyr Lys Arg Asn Leu Pro Arg Arg Gly Leu Ser Gly
                20                  25                  30

Tyr Ser Met Leu Ala Ile Gly Ile Gly Thr Leu Ile Tyr Gly His Trp
            35                  40                  45

Ser Ile Met Lys Trp Asn Arg Glu Arg Arg Leu Gln Ile Glu Asp
        50                  55                  60

Phe Glu Ala Arg Ile Ala Leu Leu Pro Leu Leu Gln Ala Glu Thr Asp
65                  70                  75                  80

Arg Arg Thr Leu Gln Met Leu Arg Glu Asn Leu Glu Glu Glu Ala Ile
                85                  90                  95

```
Ile Met Lys Asp Val Pro Asp Trp Lys Val Gly Glu Ser Val Phe His
            100                 105                 110

Thr Thr Arg Trp Val Pro Pro Leu Ile Gly Glu Leu Tyr Gly Leu Arg
        115                 120                 125

Thr Thr Glu Glu Ala Leu His Ala Ser His Gly Phe Met Trp Tyr Thr
    130                 135                 140

Gly Ser Ala Ala Ala Glu Gln Lys Leu Ile Ser Glu Glu Asp Leu Ala
145                 150                 155                 160

Ala Ala

<210> SEQ ID NO 58
<211> LENGTH: 864
<212> TYPE: DNA
<213> ORGANISM: Artificial sequence
<220> FEATURE:
<223> OTHER INFORMATION: Cell-Penetrating Peptide (CPP)-tagged AcGFP

<400> SEQUENCE: 58
atggcacatc accaccacca tcacgtgggt accggttcga atgatgacga cgacaagagt     60
ccggatagac gaaggcgcag acggaggcgt agaccgtctg ccagctatcc atacgacgtg    120
cctgactacg cgaggctgca attcatggtg agcaagggcg ccgagctgtt caccggcatc    180
gtgcccatcc tgatcgagct gaatggcgat gtgaatggcc acaagttcag cgtgagcggc    240
gagggcgagg gcgatgccac ctacggcaag ctgaccctga agttcatctg caccaccggc    300
aagctgcctg tgccctggcc caccctggtg accaccctga gctacggcgt gcagtgcttc    360
tcacgctacc ccgatcacat gaagcagcac gacttcttca gagcgccat gcctgagggc     420 tacatccagg agcgcaccat cttcttcgag gatgacggca actacaagtc gcgcgccgag    480
gtgaagttcg agggcgatac cctggtgaat cgcatcgagc tgaccggcac cgatttcaag    540
gaggatggca acatcctggg caataagatg gagtacaact acaacgccca caatgtgtac    600
atcatgaccg acaaggccaa gaatggcatc aaggtgaact tcaagatccg ccacaacatc    660
gaggatggca gcgtgcagct ggccgaccac taccagcaga taccccccat cggcgatggc    720
cctgtgctgc tgcccgataa ccactacctg tccacccaga gcgccctgtc caaggacccc    780
aacgagaagc gcgatcacat gatctacttc ggcttcgtga ccgccgccgc catcacccac    840
ggcatggatg agctgtacaa gtag                                          864

<210> SEQ ID NO 59
<211> LENGTH: 287
<212> TYPE: PRT
<213> ORGANISM: Artificial sequence
<220> FEATURE:
<223> OTHER INFORMATION: Cell-Penetrating Peptide (CPP)-tagged AcGFP

<400> SEQUENCE: 59

Met Ala His His His His His His Val Gly Thr Gly Ser Asn Asp Asp
1               5                   10                  15

Asp Asp Lys Ser Pro Asp Arg Arg Arg Arg Arg Arg Arg Arg Pro
            20                  25                  30

Ser Ala Ser Tyr Pro Tyr Asp Val Pro Asp Tyr Ala Arg Leu Gln Phe
            35                  40                  45

Met Val Ser Lys Gly Ala Glu Leu Phe Thr Gly Ile Val Pro Ile Leu
    50                  55                  60

Ile Glu Leu Asn Gly Asp Val Asn Gly His Lys Phe Ser Val Ser Gly
65                  70                  75                  80
```

-continued

```
Glu Gly Glu Gly Asp Ala Thr Tyr Gly Lys Leu Thr Leu Lys Phe Ile
            85                      90                  95
Cys Thr Thr Gly Lys Leu Pro Val Pro Trp Pro Thr Leu Val Thr Thr
            100             105                 110
Leu Ser Tyr Gly Val Gln Cys Phe Ser Arg Tyr Pro Asp His Met Lys
        115                 120                 125
Gln His Asp Phe Phe Lys Ser Ala Met Pro Glu Gly Tyr Ile Gln Glu
        130                 135                 140
Arg Thr Ile Phe Phe Glu Asp Asp Gly Asn Tyr Lys Ser Arg Ala Glu
145                 150                 155                 160
Val Lys Phe Glu Gly Asp Thr Leu Val Asn Arg Ile Glu Leu Thr Gly
                165                 170                 175
Thr Asp Phe Lys Glu Asp Gly Asn Ile Leu Gly Asn Lys Met Glu Tyr
            180                 185                 190
Asn Tyr Asn Ala His Asn Val Tyr Ile Met Thr Asp Lys Ala Lys Asn
        195                 200                 205
Gly Ile Lys Val Asn Phe Lys Ile Arg His Asn Ile Glu Asp Gly Ser
        210                 215                 220
Val Gln Leu Ala Asp His Tyr Gln Gln Asn Thr Pro Ile Gly Asp Gly
225                 230                 235                 240
Pro Val Leu Leu Pro Asp Asn His Tyr Leu Ser Thr Gln Ser Ala Leu
                245                 250                 255
Ser Lys Asp Pro Asn Glu Lys Arg Asp His Met Ile Tyr Phe Gly Phe
            260                 265                 270
Val Thr Ala Ala Ala Ile Thr His Gly Met Asp Glu Leu Tyr Lys
        275                 280                 285
```